(12) United States Patent
Marmor

(10) Patent No.: US 10,172,539 B2
(45) Date of Patent: *Jan. 8, 2019

(54) DETERMINING AN AMOUNT OF REPERFUSION IN MYOCARDIUM AND ASSESSING EFFECTIVENESS OF THROMBOLYSIS

(71) Applicant: CORSENS MEDICAL LTD., Tel Aviv (IL)

(72) Inventor: Alon Marmor, Kfar Hanania (IL)

(73) Assignee: CORSENS MEDICAL LTD., Tel Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/691,796

(22) Filed: Aug. 31, 2017

(65) Prior Publication Data

US 2018/0055419 A1    Mar. 1, 2018

Related U.S. Application Data

(63) Continuation-in-part of application No. 14/880,283, filed on Oct. 12, 2015, now Pat. No. 10,028,677.

(51) Int. Cl.
*A61B 5/11* (2006.01)
*A61B 5/02* (2006.01)
(Continued)

(52) U.S. Cl.
CPC ........ *A61B 5/1102* (2013.01); *A61B 5/02028* (2013.01); *A61B 5/0452* (2013.01); *A61B 5/4824* (2013.01); *A61B 5/4848* (2013.01); *A61B 5/6831* (2013.01); *A61B 5/7275* (2013.01); *A61B 5/7278* (2013.01); *A61B 5/7282* (2013.01); *G06F 19/00* (2013.01); *A61B 5/746* (2013.01); *A61B 8/485* (2013.01); (Continued)

(58) Field of Classification Search
CPC ....... A61B 5/11; A61B 5/6831; A61B 5/7275; A61B 5/4824; A61B 5/02028; A61B 5/7278; A61B 2505/01; A61B 2562/0219
See application file for complete search history.

(56) References Cited

U.S. PATENT DOCUMENTS

2014/0107505 A1* 4/2014 Marmor .................. A61B 7/00
                                                                600/486

* cited by examiner

*Primary Examiner* — Christopher D Koharski
*Assistant Examiner* — Roland Dinga
(74) *Attorney, Agent, or Firm* — Mark M. Friedman

(57) ABSTRACT

Quantitatively determining an amount of reperfusion in an artery after angioplasty and quantitatively assessing an effectiveness of thrombolysis by non-invasively sensing from outside the subject mechanical vibrations from a mechanical contraction of at least one ventricle to simultaneously measure (a) IVCT (time duration of an isovolumetric contraction portion of a systole phase) and (b) a peak endocardial acceleration (PEA) during the IVCT. PEA is measured before and after opening the artery (or before and after thrombolysis) and in some embodiments one calculates a myocardial contractility index (MCI) of the subject, for example MCI=PEA/IVCT. A determination unit compares the first and second PEA (or the first and second MCI), and then determines an amount of reperfusion based on the comparison. The amount of reperfusion is proportionate to a viable myocardium and, in the case of thrombolysis, the amount of reperfusion quantitatively assesses the effectiveness of thrombolysis.

4 Claims, 24 Drawing Sheets

(51) Int. Cl.
  *A61B 5/00* (2006.01)
  *A61B 5/0452* (2006.01)
  *G06F 19/00* (2018.01)
  *A61B 8/08* (2006.01)
(52) U.S. Cl.
  CPC ... *A61B 2505/01* (2013.01); *A61B 2562/0204* (2013.01); *A61B 2562/0219* (2013.01)

| Patient ID | Patient Name | Test Date | Test Time | PEA Before Ischemia | PEA In Ischemia | % of decreasing PEA | PEA After Ischemia | MCI Before Ischemia |
|---|---|---|---|---|---|---|---|---|
| CS-02 | E P | 21-Jan-15 | 16:26 | 14225 | 12121 | 15 | 14587 | 512 |
| CS-04 | H S | 26-Jan-15 | 16:02 | 12270 | 9838 | 20 | 10294 | 435 |
| CS-06 | L E | 26-Jan-15 | 17:56 | 42305 | 19055 | 55 | 44779 | 1320 |
| CS-07 | Z Y | 26-Jan-15 | 19:03 | 24086 | 16137 | 33 | 26367 | 574 |
| CS-10 | S M | 2-Feb-15 | 17:26 | 26114 | 23266 | 11 | 26367 | 751 |
| CS-12 | A S | 2-Feb-15 | 19:29 | 24299 | 19140 | 21 | 23620 | 672 |
| CS-14 | B F | 4-Feb-15 | 17:12 | 19910 | 13745 | 31 | 18758 | 983 |
| CS-15 | A Y | 9-Feb-15 | 16:25 | 20323 | 18469 | 9 | 20487 | 961 |
| CS-17 | M F | 11-Feb-15 | 15:48 | 41873 | 33837 | 19 | 42399 | 1972 |
| CS-22 | B G | 23-Feb-15 | 19:13 | 23935 | 15039 | 37 | 18208 | 749 |
| CS-30 | F Z | 2-Mar-15 | 19:07 | 17740 | 14514 | 18 | 12715 | 510 |
| CS-33 | S M | 9-Mar-15 | 16:01 | 15610 | 15222 | 2 | 17944 | 506 |
| CS-34 | S R | 9-Mar-15 | 17:01 | 17907 | 14013 | 22 | 21260 | 831 |
| CS-35 | N T | 9-Mar-15 | 18:07 | 34606 | 15563 | 55 | 30843 | 1866 |
| CS-36 | F Y | 9-Mar-15 | 19:09 | 20294 | 16735 | 18 | 21504 | 881 |
| CS-42 | E Z | 16-Mar-15 | 16:49 | 21736 | 18115 | 17 | 19653 | 758 |
| CS-44 | P M | 23-Mar-15 | 16:53 | 15316 | 7104 | 54 | 10965 | 967 |
| CS-45 | K V | 23-Mar-15 | 17:56 | 38541 | 32849 | 15 | 38065 | 1241 |
| CS-53 | P V | 1-Apr-15 | 15:34 | 33485 | 26965 | 19 | 31962 | 1169 |
| CS-55 | B A | 15-Apr-15 | 17:03 | 35214 | 26049 | 26 | 35685 | 1395 |
| CS-57 | A F | 20-Apr-15 | 18:31 | 13093 | 9106 | 30 | 15991 | 449 |
| CS-59 | S E | 20-Apr-15 | 19:22 | 11628 | 11071 | 5 | 12939 | 578 |
| CS-62 | S O | 4-May-15 | 16:37 | 22840 | 13671 | 40 | 16642 | 337 |
| CS-63 | N V | 4-May-15 | 17:34 | 19550 | 14916 | 24 | 22399 | 1026 |
| CS-67 | V F | 20-May-15 | 16:48 | 11805 | 9594 | 19 | 11515 | 243 |
| CS-68 | D M | 26-May-15 | 18:10 | 11052 | 8947 | 19 | 9969 | 364 |
| CS-71 | A N | 22-Jun-15 | 17:34 | 24210 | 20800 | 14 | 23417 | 602 |

FIG. 14

| MCl In Ischemia | % of decreasing MCl | MCl After Ischemia |
|---|---|---|
| 346 | 32 | 533 |
| 252 | 42 | 651 |
| 500 | 62 | 1399 |
| 391 | 32 | 608 |
| 673 | 10 | 701 |
| 398 | 41 | 472 |
| 567 | 42 | 1052 |
| 879 | 9 | 933 |
| 1291 | 35 | 2195 |
| 196 | 74 | 649 |
| 441 | 14 | 407 |
| 487 | 4 | 482 |
| 544 | 35 | 866 |
| 817 | 56 | 1298 |
| 598 | 32 | 1166 |
| 602 | 21 | 562 |
| 619 | 36 | 807 |
| 1086 | 12 | 1584 |
| 892 | 24 | 1206 |
| 833 | 40 | 1257 |
| 351 | 22 | 420 |
| 357 | 38 | 634 |
| 198 | 41 | 295 |
| 520 | 49 | 983 |
| 202 | 17 | 205 |
| 271 | 26 | 307 |
| 425 | 29 | 629 |

FIG. 14 (continued)

DETERMINING AN AMOUNT OF REPERFUSION IN MYOCARDIUM AND ASSESSING EFFECTIVENESS OF THROMBOLYSIS

FIELD AND BACKGROUND OF THE INVENTION

The invention is in the field of medical diagnosis of cardiac problems.

After a heart attack, a common procedure is to open the coronary artery through angioplasty. An ECG can identify a location of cardiac damage but not quantify it. Even invasively opening an artery in the heart through urgent angioplasty cannot determine the extent to which the myocardium has died. One problem is determining quantitatively the amount of reperfusion that has occurred in the myocardium after opening the coronary artery after the heart attack as well as determining the amount of restoration of function in the subject's heart after the heart attack. A parallel problem is determining, after the artery has been opened, an amount of viable or salvageable heart muscle after a heart attack occurs. Even after opening the cardiac artery one cannot determine the extent that the heart muscle has died and quantifying the severity of a heart attack (i.e. severe, moderate, light). Knowing this affects prognosis and treatment for the patient. A further problem is deciding when to discontinue administration of thrombolysis, especially based on a quantitative determination.

In addition, when a patient goes to the emergency room reporting chest pain, an ECG and a cardiac enzyme test are performed. It is widely recognized, however, that normal ECG and negative enzyme test results will result in 24 hour patient hospitalization as a precaution. Since 80% of patients who report to the hospital emergency room with chest pain have chest pain that is not cardiac related, current clinical practice results in many unnecessary hospitalizations.

There is therefore a compelling need to have improved methods, apparatuses and/or systems for accurate diagnosis of cardiac related chest pain and there is a compelling need to have accurate diagnostics for other cardiac related issues.

SUMMARY OF THE INVENTION

One aspect of the invention is a non-invasive apparatus configured to non-invasively determine an amount of reperfusion of blood to a myocardium supplied by an artery of a mammalian subject after a heart attack of the mammalian subject, the apparatus comprising a sensor unit configured to non-invasively sense from outside the subject mechanical vibrations that are from a mechanical contraction of at least one of the ventricles of the heart of the mammalian subject so as to simultaneously measure (a) IN/CT, wherein IVCT is a time duration of an isovolumetric contraction portion of a systole phase of a cardiac cycle of the subject; and (b) a peak endocardial acceleration (PEA) of the heart of the subject during the IVCT; and a determination unit comprising one or more processors programmed by software stored on a memory, the determination unit configured to receive digital signals corresponding to the sensed mechanical vibrations, and to determine the PEA during the IVCT, the determination unit including a perfusion module for determining, by the one or more processors, an amount of reperfusion in the myocardium by comparing a first PEA of the subject sensed by the sensor unit after a heart attack but before opening the artery to a second PEA of the subject sensed by the sensor unit at a subsequent time after opening the artery, said amount of reperfusion being proportionate to a viable myocardium supplied by the artery.

Another aspect of the invention is a method of non-invasively determining an amount of reperfusion in a myocardium supplied by an artery of a mammalian subject after a heart attack of the mammalian subject, comprising after a heart attack but before opening the artery non-invasively sensing by a device positioned outside the subject mechanical vibrations that are from a mechanical contraction of at least one of the ventricles of the heart of the mammalian subject, so as to measure a first peak endocardial acceleration (PEA) of the heart of the subject during an IVCT wherein IVCT is a time duration of an isovolumetric contraction portion of a systole phase of a cardiac cycle of the subject; after opening the artery after the heart attack, non-invasively sensing by a device positioned outside the subject mechanical vibrations that are from a mechanical contraction of at least one of the ventricles of the heart of the mammalian subject, so as to measure a second peak endocardial acceleration (PEA) of the heart of the subject during an IVCT; and determining, by one or more processors, an amount of reperfusion in the myocardium by comparing an amount by which the second PEA exceeds the first PEA, said amount of reperfusion being proportionate to a viable myocardium supplied by the artery.

A still further aspect of the invention is a non-invasive apparatus configured to non-invasively determine an amount of reperfusion of blood to a myocardium supplied by an artery of a mammalian subject after a heart attack of the mammalian subject, the apparatus comprising a sensor unit configured to non-invasively sense from outside the subject mechanical vibrations that are from a mechanical contraction of at least one of the ventricles of the heart of the mammalian subject so as to simultaneously measure (a) IVCT, wherein IVCT is a time duration of an isovolumetric contraction portion of a systole phase of a cardiac cycle of the subject; and (b) a peak endocardial acceleration (PEA) of the heart of the subject during the IVCT; and a determination unit comprising one or more processors programmed by software stored on a memory, the determination unit configured to receive digital signals corresponding to the sensed mechanical vibrations, and to determine the PEA during the IVCT, the one or more processors configured to also calculate a first myocardial contractility index (MCI) of the subject such that MCI comprises a ratio of the PEA of the subject to the IVCT of the subject; the determination unit including a perfusion module for determining, by the one or more processors, an amount of reperfusion in the myocardium by comparing a first MCI of the subject sensed by the sensor unit after a heart attack but before opening the artery to a second MCI of the subject sensed by the sensor unit at a subsequent time after opening the artery, said amount of reperfusion being proportionate to a viable myocardium supplied by the artery.

Another aspect of the invention is a method of non-invasively determining an amount of reperfusion in a myocardium supplied by an artery of a mammalian subject after a heart attack of the mammalian subject, comprising after a heart attack but before opening the artery non-invasively sensing by a device positioned outside the subject mechanical vibrations that are from a mechanical contraction of at least one of the ventricles of the heart of the mammalian subject, so as to simultaneously measure a first IVCT, wherein IVCT is a time duration of an isovolumetric contraction portion of a systole phase of a cardiac cycle of the subject, and a first peak endocardial acceleration (PEA) of the heart of the subject during the first IVCT; calculating, by one or more processors, a first myocardial contractility index (MCI) of the subject, wherein the first MCI comprises a ratio of the first PEA of the subject to the first IVCT of the subject; after opening the artery after the heart attack, non-invasively sensing by a device positioned outside the subject mechanical vibrations that are from a mechanical contraction of at least one of the ventricles of the heart of the mammalian subject, so as to simultaneously measure a second IVCT and a second peak endocardial acceleration (PEA) of the heart of the subject during the second IVCT; calculating, by one or more processors, a second myocardial contractility index (MCI) of the subject wherein the second MCI comprises a ratio of the second PEA of the subject to the second IVCT of the subject; and determining, by one or more processors, an amount of reperfusion in the myocardium, by comparing an amount by which the second MCI exceeds the first MCI, said amount of reperfusion being proportionate to a viable myocardium supplied by the artery.

A still further aspect of the invention is a non-invasive apparatus configured to non-invasively assess an effectiveness of thrombolysis on a clot in an artery of a mammalian subject after a heart attack of the mammalian subject by determining an amount of reperfusion in the artery, the apparatus comprising a sensor unit configured to non-invasively sense from outside the subject mechanical vibrations that are from a mechanical contraction of at least one of the ventricles of the heart of the mammalian subject so as to simultaneously measure (a) IVCT, wherein IVCT is a time duration of an isovolumetric contraction portion of a systole phase of a cardiac cycle of the subject; and (b) a peak endocardial acceleration (PEA) of the heart of the subject during the IVCT; and a determination unit comprising one or more processors programmed by software stored on a memory, the determination unit configured to receive digital signals corresponding to the sensed mechanical vibrations, and to determine the PEA during the IVCT, the determination unit including a perfusion module for determining, by the one or more processors, an amount of reperfusion in the artery by comparing a first PEA of the subject sensed by the sensor unit after a heart attack but before the thrombolysis to a second PEA of the subject sensed by the sensor unit after the thrombolysis, said amount of reperfusion determining an assessment of the effectiveness of the thrombolysis.

Another aspect of the invention is a method of non-invasively assessing an effectiveness of thrombolysis on a clot in an artery of a mammalian subject after a heart attack of the mammalian subject by determining an amount of reperfusion in the artery, comprising after a heart attack but before thrombolysis, non-invasively sensing by a device positioned outside the subject mechanical vibrations that are from a mechanical contraction of at least one of the ventricles of the heart of the mammalian subject, so as to measure a first peak endocardial acceleration (PEA) of the heart of the subject during an IVCT wherein IVCT is a time duration of an isovolumetric contraction portion of a systole phase of a cardiac cycle of the subject; after the thrombolysis to dissolve the clot, non-invasively sensing by a device positioned outside the subject mechanical vibrations that are from a mechanical contraction of at least one of the ventricles of the heart of the mammalian subject, so as to measure a second peak endocardial acceleration (PEA) of the heart of the subject during an IVCT; and determining, by one or more processors, an amount of reperfusion in the artery by comparing an amount by which the second PEA exceeds the first PEA, said amount of reperfusion determining an assessment of the effectiveness of the thrombolysis.

A further aspect of the invention is a non-invasive apparatus configured to non-invasively assess an effectiveness of thrombolysis on a clot in an artery of a mammalian subject after a heart attack of the mammalian subject by determining an amount of reperfusion in the artery, the apparatus comprising a sensor unit configured to non-invasively sense from outside the subject mechanical vibrations that are from a mechanical contraction of at least one of the ventricles of the heart of the mammalian subject so as to simultaneously measure (a) IVCT, wherein IVCT is a time duration of an isovolumetric contraction portion of a systole phase of a cardiac cycle of the subject; and (b) a peak endocardial acceleration (PEA) of the heart of the subject during the IVCT; and a determination unit comprising one or more processors programmed by software stored on a memory, the determination unit configured to receive digital signals corresponding to the sensed mechanical vibrations, and to determine the PEA during the IVCT, the one or more processors configured to also calculate a first myocardial contractility index (MCI) of the subject such that MCI comprises a ratio of the PEA of the subject to the IVCT of the subject; the determination unit including a perfusion module for determining, by the one or more processors, an amount of reperfusion in the artery by comparing a first MCI of the subject sensed by the sensor unit after a heart attack but before the thrombolysis to a second MCI of the subject sensed by the sensor unit after the thrombolysis, said amount of reperfusion determining an assessment of the effectiveness of the thrombolysis.

A still further aspect of the invention is a method of non-invasively assessing an effectiveness of thrombolysis on a clot in an artery of a mammalian subject after a heart attack of the mammalian subject by determining an amount of reperfusion in the artery, comprising after a heart attack but before thrombolysis, non-invasively sensing by a device positioned outside the subject mechanical vibrations that are from a mechanical contraction of at least one of the ventricles of the heart of the mammalian subject, so as to simultaneously measure a first IVCT, wherein IVCT is a time duration of an isovolumetric contraction portion of a systole phase of a cardiac cycle of the subject, and a first peak endocardial acceleration (PEA) of the heart of the subject during the first IVCT; calculating, by one or more processors, a first myocardial contractility index (MCI) of the subject, wherein the first MCI comprises a ratio of the first PEA of the subject to the first IVCT of the subject; after the thrombolysis to dissolve the clot, non-invasively sensing by a device positioned outside the subject mechanical vibrations that are from a mechanical contraction of at least one of the ventricles of the heart of the mammalian subject, so as to simultaneously measure a second IVCT and a second peak endocardial acceleration (PEA) of the heart of the subject during the second IVCT; calculating, by one or more processors, a second myocardial contractility index (MCI) of the subject wherein the second MCI comprises a ratio of the second PEA of the subject to the second IVCT of the subject; and determining, by one or more processors, an amount of reperfusion in the artery by comparing an amount by which the second MCI exceeds the first MCI, said amount of reperfusion determining an assessment of the effectiveness of the thrombolysis.

These and other features, aspects and advantages of the invention will become better understood with reference to the following drawings, descriptions and claims.

BRIEF DESCRIPTION OF THE DRAWINGS

Various embodiments are herein described, by way of example only, with reference to the accompanying drawings, wherein:

FIG. 14 shows an EXCEL file summary of the results of the 27 subjects enrolled in the study conducted in accordance with one embodiment of the invention;

DETAILED DESCRIPTION OF THE INVENTION

Figure 1:
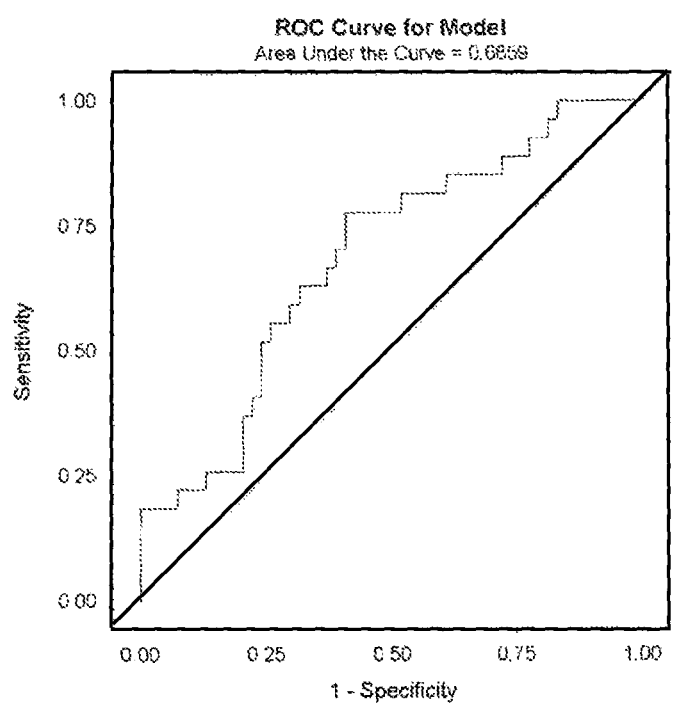
FIG. 1 is a graph of an ROC curve with AUC for PEA discrimination ability between ischemia related chest pain and non-ischemia related chest pain, in accordance with one embodiment of the invention.

The following detailed description is of the best currently contemplated modes of carrying out the invention. The description is not to be taken in a limiting sense, but is made merely for the purpose of illustrating the general principles of the invention.

The invention generally provides methods, apparatus and/or systems for medical diagnosis of cardiac issues in a mammalian subject, for example a human, including but not limited to determining a quantitative amount of reperfusion in the myocardium after opening the artery, such as by angioplasty, a quantitative assessment of the amount of restoration of function of the heart after opening the artery, a quantitative assessment of the effectiveness of thrombolysis (for example whether or not it has been effective in order to decide if it (i.e. medication) can be discontinued) based on an amount of reperfusion in the artery, an amount of viable or salvageable myocardium that remains after a heart attack. The invention also provides methods, apparatus and/or systems of quantitatively differentially diagnosing between cardiac related and non-cardiac related chest pain in a mammalian subject, for example a human, including in some embodiments doing so dynamically; determining, for example quantitatively, if total occlusion of an artery, for example a coronary artery, has occurred, quantitatively determining myocardial infarction. The invention uses in some embodiments a new parameter called a myocardial contractility index (MCI) that in some embodiments comprises a ratio of the Peak Endocardial Acceleration (PEA) of the subject to the IVCT of the subject. In one embodiment, MCI=PEA/IVCT.

One problem in cardiology is determining the amount of viable or salvageable heart muscle after a heart attack occurs. Another related problem is quantitatively assessing an amount of reperfusion that has occurred after opening an artery after a heart attack (i.e. using angioplasty). Even after opening the cardiac artery one cannot determine the extent that the heart muscle has died or quantify the severity of a heart attack (i.e. severe, moderate, light). Knowing this affects prognosis and treatment for the patient. A further problem is deciding when to discontinue administration of thrombolysis, especially based on a quantitative determination. Another challenge is a quantitatively determining whether total occlusion of a coronary artery has occurred. A further challenge is quantitatively determining Whether a myocardial infarction has occurred. One further major problem in cardiology, especially emergency cardiology, is differentiating between cardiac related chest pain, called ischemia, and non-cardiac related chest pain. It is especially challenging to make such a differentiation quantitatively. A further problem is unnecessary precautionary hospitalizations of patients admitted to emergency rooms with chest pains after the patient is tested negatively for the presence of enzymes from necrosis and after ECG does not indicate a heart attack.

The invention, in some embodiments, differentially diagnoses whether chest pain of a subject is cardiac related or is not cardiac related. In some embodiments, the invention reaches a determination whether the chest is cardiac related (or whether the chest pain is suspected of being cardiac related in other embodiments) and does so quantitatively, which is very useful for emergency cardiology. Moreover, in some embodiments, the determination that the chest pain is cardiac-related is very strong due to the sensing, calculating, comparing and determining steps (and in the case of PEA without the calculating step) being repeated dynamically to show that the decline in MCI or PEA continues even further (whereas in non-cardiac chest pain the MCI and PEA remain the same or even increase). In some embodiments of the invention, a quantitative determination that chest pain is cardiac related or not is made, and in some embodiments the quantitative determination is made without the need for an expert to interpret the results. In certain embodiments, this determination allows patients who are distant from emergency rooms, or distant from doctors, to have such a determination made without consulting an expert.

The invention in some embodiments non-invasively quantities whether a victim of a heart attack sustained light, medium of severe damage from a heart attack. The invention, in some embodiments, quantitatively determines an amount of reperfusion that has occurred after opening the artery through angioplasty. The invention also quantitatively determines an amount of restoration of function of the heart after opening the artery. For example, in some embodiments, the determined increase in MCI or PEA after the artery is opened is proportionate to the amount of living healthy heart muscle remaining in the patient. Accordingly, certain embodiments of the invention yield a measure of contractile reserve in the patient, which has great importance regarding the future of the patient. Conversely, occluding a coronary artery, for example during routine stent implantation, produces a decrease in PEA and MCI due to ischemia. When the myocardium supplied by the artery being occluded is dead no change in PEA or MCI occurs. In some embodiments, the invention yields a measure of a decrease in MCI and PEA during occlusion, which has great importance, since if there is viable myocardium it can be saved and the function improved by a bypass operation, etc.

It is important to assess, especially quantitatively, the effectiveness of thrombolysis, in which medication for dissolving the artery clot is administered. This involves assessing whether the thrombolysis has successfully dissolved the clot in the artery to a level of certainty that allows doctor to comfortably discontinue the medication. Some embodiments of the invention allows one to determine, in some embodiments quantitatively, that thrombolysis has been effective, for example by measuring an increase in the MCI or the PEA after the thrombolysis (relative to before the thrombolysis) and comparing the measured increase to a predetermined amount of increase. The increase in PEA or MCI indicates reperfusion of blood in the artery and this is quantified in some embodiments. Knowing this is important since the medication used for thrombolysis has a side effect of hemorrhage, and also because thrombolysis is not totally reliable at achieving success. Therefore, knowing when to discontinue the medication creates an important medical benefit.

The invention, in certain embodiments, is capable of detecting a total occlusion of a coronary artery in a mammalian subject, for example if the MCI or the PEA of the subject declined by at least a predetermined amount relative to a baseline MCI or PEA. The invention, in some embodiments, utilizes MCI, or myocardial contractility index, which comprises a ratio between PEA (peak endocardial acceleration) and IVCT, the duration of the isovolumetric contraction portion of a systole phase of a cardiac cycle of a subject, wherein in some embodiments the ratio is PEA/IVCT. By utilizing an index such as MCI as the measured parameter, which index is proportional to two different parameters (PEA and the inverse of IVCT) that are each affected by occlusion, (PEA decreased and IVCT is increased such that an inverse of IVCT is decreased) the invention in some embodiments utilizes a parameter is more sensitive to changes brought about by occlusion of an artery of the heart. Certain embodiments of the invention are usable at home and are usable for example without any professional interpretations. For example, in the emergency room, the PEA of the patient would have already declined to its lowest point in many cases since patients often reach the emergency room only several hours after the initial insult, i.e. several hours after chest pain started. Therefore, no dynamic measurement of PEA or calculation of MCI is possible in these cases (these parameters are in any event not measured or calculated today to diagnose the case of the chest pain). However, at home, dynamic measurement of MCI and PEA is possible and useful in some embodiments of the invention. The invention reaches the determinations described herein non-invasively, and in some embodiments, without interpretations by an expert.

The principles and operation of a system/apparatus and method for Determining an Amount of Reperfusion in Myocardium and a system/apparatus and method for Assessing Effectiveness of Thrombolysis, according to the invention may be better understood with reference to the drawings and the accompanying description.

In the methods and apparatuses of the invention where there is a baseline MCI of the subject or an appropriate population of subjects, when comparing the MCI of the subject to the baseline MCI (a circumstance that is generally not applicable to embodiments herein that measure reperfusion or that assess the effectiveness of thrombolysis since in both those cases there is no precise baseline other than the first MCI or the first PEA as a reference compared to the second MCI or second PEA), the baseline MCI is defined as one of (i) the baseline MCI of the subject, and (ii) a representative value of the baseline MCI of a population of subjects less a predetermined value. The predetermined value is, in some embodiments, a predetermined number of standard deviations, for example two standard deviations (2SD), from the representative value of the baseline MCI of the population of subjects. The representative value (for example a mean, median, average or other representative value) is for example a normal value, for example a mean normal value, of the baseline MCI of the population of subjects. Similarly, when comparing the PEA of the subject to a baseline PEA (a circumstance that is generally not applicable to embodiments herein that measure reperfusion or that assess the effectiveness of thrombolysis since in both those cases there is no precise baseline other than the first PEA or first MCI as a reference to compare to the second PEA or second MCI), the baseline PEA is defined as one of (i) the baseline PEA of the subject, and (ii) a representative value of the baseline PEA of a population of subjects less a predetermined value. The predetermined value is for example a predetermined number of standard deviations, for example two standard deviations (2SD), from the representative value (for example a mean, median, average or other representative value) which for example is normal value, i.e. a mean normal value, of the baseline PEA of the population of subjects. In one example, the predetermined value is two standard deviations from a mean normal value of a baseline PEA of the population of subjects. In this example, if the values of the PEA of a population of 70 subjects has a normal distribution whose representative value (for example a mean, median, average or other representative value) is 20,000 in units of acceleration such as dP/dtmax (or an equivalent number in units of G or milig), and if the predetermined value is two standard deviations, then if the standard deviation is plus or minus 3,000, the number 6,000 is the predetermined value and the number 14,000 represents the representative value of the baseline PEA of the population of subjects less the predetermined value. Note that since a decline and not an increase in MCI or PEA is being measured, the representative value minus the 2SD (not plus the 2SD) is utilized.

The reason that two standard deviations, or some other predetermined value, is subtracted from the representative value to formulate the "baseline MCI" or to formulate the "baseline PEA", when comparisons are made (in any method or apparatus or system of the invention) to a population of subjects, instead of simply using the representative value itself, is simply in order to be cautious in reaching the determination involved (for example a determination that the chest pain is cardiac related). Accordingly, other examples of suitable predetermined values subtracted from the representative value of the baseline MCI (or baseline PEA) are also appropriate in certain embodiments other than two SD, such as one SD or zero SD or another number of SDs (or a different suitable predetermined value). For example if one is interested for whatever reason in enduring greater risk and using less caution, in one example the predetermined value utilized is zero and the representative value of the baseline MCI (or PEA) of the population of subjects less the predetermined value is simply the representative value.

Applicant has conducted an experiment to measure the ability of MCI, wherein MCI=PEA divided by IVCT, to quantitatively detect ischemic episodes and achieve other cardiac diagnostics (including not limited to amount of reperfusion, amount of viable myocardium and effectiveness of thrombolysis). 60 to 70 human patients had arteriosclerosis and needed stent implantation. Before the stent implantation, a balloon was placed in the coronary artery as part of the routine. IVCT and PEA were measured simultaneously using an apparatus of the invention adapted to be attached to the chest of the patient.

Statistical Summary of Data from Applicant's Study

A statistical analysis performed on preliminary data from a study conducted by Applicant is presented. The objective of the study was to assess whether, by analyzing the change from baseline in MCI or PEA, ischemic episodes induced by balloon inflation can be detected. Subjects who are scheduled to undergo diagnostic catheterization, after analyzing the angiography the cardiologist in charge will decide if a stent should be implanted in a proximal or mid arterial place. If this is the case the patient is eligible for the trial. The patient signs an informed consent for study participation before the beginning of the catheterization. The elastic belt is placed on the patient without closing it on the chest. After the cardiologist places the stent and prior to inflating the balloon the elastic belt is closed on the chest of the patient and continuous recording of the signals is performed during balloon inflation for 25 sec, and during deflation, for a total of 2 minutes. The elastic belt is then removed and the study is completed. The study endpoints include peak acceleration value (PEA) and MCI Index—calculated by the device's mathematical algorithm.

The required significance level of findings will be equal to or lower than 5%. All statistical tests will be two-sided. Where confidence limits are appropriate, the confidence level will be 95%. All statistical analyses are performed using SAS v9.3 (SAS®, SAS Institute Cary, N.C. USA) software. PEA, MCI and the % change from baseline PEA and MCI values will be summarized by a mean, standard deviation, minimum, median and maximum. PEA and MCI values are compared between the three different time points, with a paired t-test. The % change from baseline in PEA is tested to see if it is lower than −10%, with a t-test. The % change from baseline in MCI is tested to see if it is lower than −20%, with a t-test. As a preliminary indication of whether PEA and MCI can discriminate between Ischemia and No-Ischemia and ROC analysis is performed using the log-transformed values of both. PEA and MCI, logistic regression is also performed to calculate the odds ratios of detection of Ischemia with each of the variables. Finally a sample size is calculated to test the hypothesis that PEA % reduction is greater than 20%, and MCI greater than 30%.

A total number of 27 subjects were enrolled in the study and has data available for the interim analysis. FIG. 14 shows an EXCEL file summary of the results of the 27 subjects enrolled in the study. The total study was 60-70 subjects.

Table 1 shows the distribution of PEA before, during and after Ischemia, and Table 2 shows the statistical comparison of the time points pairs of PEA. We find that in ischemia PEA is statistically significantly (p<0.0001) lower than before ischemia. Once the balloon is deflated the PEA levels return to their baseline values, since the difference before to after is not significantly different from zero (p=0.3002)

Table 3 shows the distribution of the percent decrease in PEA from baseline during ischemia, where we see that all patients had a decrease in PEA with the percentage ranging between 2.5% up to a 55% decrease. The mean reduction of 23.99% (SD=14.08%) was found statistically significantly greater than 10% (p<0.0001, Table 4). The odds ratio for detection of ischemia with PEA is 0.178 (p=0.0078), this means that for every unit decrease in log-PEA the risk of ischemia is 5.6 times (1/0.178) higher (Table 5). FIG. 1 show the diagnostic accuracy in terms of the ROC curve and its summary measure the AUC (area under the curve) which equals 0.68 (low-moderate discriminatory power), this indicates a potential for discrimination.

TABLE 1

Distribution of PEA before, during and after Ischemia

|  | PEA Before Ischemia | PEA In Ischemia | PEA After Ischemia |
| --- | --- | --- | --- |
| N | 27 | 27 | 27 |
| Mean | 22740 | 16884 | 22198 |
| SD | 9343.4 | 6857.4 | 9709.6 |
| Min | 11052 | 7104.0 | 9969.0 |
| Median | 20323 | 15222 | 20487 |
| Max | 42305 | 33837 | 44779 |

TABLE 2

Comparison of PEA before to during and before to after Ischemia, mean difference with 95% confidence interval and p-value of paired t-test.

|  | Mean | 95% CL Mean | | P-value |
| --- | --- | --- | --- | --- |
| Before-During | 5855.0 | 3814.9 | 7895.2 | <0.0001 |
| Before-After | 542.0 | −511.9 | 1595.8 | 0.3002 |

TABLE 3

Distribution of PEA % change from baseline to Ischemia

|  | % Change PEA |
|---|---|
| N | 27 |
| Mean | −23.99% |
| SD | 14.08% |
| Min | −55.03% |
| Median | −19.47% |
| Max | −2.49% |

TABLE 4 t-test of PEA % change from baseline to Ischemia, mean with 95% confidence interval.

| Mean | 95% CL Mean | | P-value |
|---|---|---|---|
| −23.99% | −29.56% | −18.42% | <0.0001 |

TABLE 5

Odds ratio for the effect of PEA (log-transformed) in differentiating between ischemia and no-ischemia with level of significance 95% confidence interval

| Odds Ratio | 95% Wald Confidence Limits | | P-value |
|---|---|---|---|
| 0.178 | 0.050 | 0.634 | 0.0078 |

Table 6 shows the distribution of MCI before during and after Ischemia, and Table 7 the statistical comparison of the time points pairs of MCI. We find that in ischemia MCI is statistically significantly (p<0.0001) lower than before ischemia. Once the balloon is deflated the PEA levels return to their baseline values, since the difference before to after is not significantly different from zero (p=0.7014)

Figure 2:
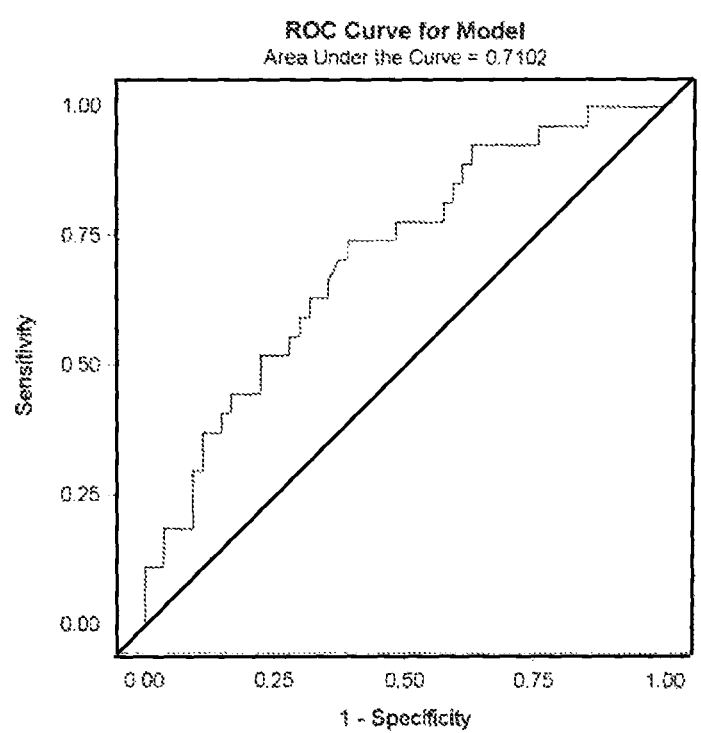
FIG. 2 is a graph of an ROC curve with AUC for MCI discrimination ability between ischemia related chest pain and non-ischemia related chest pain, in accordance with one embodiment of the invention.

Table 8 shows the distribution of the percent decrease in MCI from baseline during ischemia, where we see that all patients had a decrease in PEA with the percentage ranging between 3.75% up to a 73% decrease. The mean reduction of 32.39% (SD=16.6%) was found statistically significantly greater than 20% (p=0.0006, Table 9). The odds ratio for detection of ischemia with MCI is 0.225 (p=0.0031), this means that for every unit decrease in log-MCI the risk of ischemia is 4.4 times (1/0.225) higher (Table 9). FIG. 2 shows the diagnostic accuracy in terms of the ROC curve and its summary measure the AUC which equals 0.71 (low-moderate discriminatory power), this indicates a potential for discrimination.

TABLE 6

Distribution of MCI before, during and after Ischemia

|  | MCI Before Ischemia | MCI In Ischemia | MCI After Ischemia |
|---|---|---|---|
| N | 27 | 27 | 27 |
| Mean | 838.96 | 545.78 | 825.96 |
| SD | 436.65 | 275.71 | 456.24 |
| Min | 243.00 | 196.00 | 205.00 |
| Median | 751.00 | 500.00 | 651.00 |
| Max | 1972.0 | 1291.0 | 2195.0 |

TABLE 7

Comparison of MCI before to during and before to after Ischemia, mean difference with 95% confidence interval and p-value of paired t-test.

|  | Mean | 95% CL Mean | | P-value |
|---|---|---|---|---|
| Before-During | 293.2 | 192.6 | 393.8 | <0.0001 |
| Before-After | 13.00 | −55.91 | 81.91 | 0.7014 |

TABLE 8

Distribution of MCI % change from baseline to Ischemia

|  | % Change MCI |
|---|---|
| N | 27 |
| Mean | −32.39% |
| SD | 16.60% |
| Min | −73.83% |
| Median | −32.42% |
| Max | −3.75% |

TABLE 9 t-test of MCI % change from baseline to Ischemia, mean with 95% confidence interval.

| Mean | 95% CL Mean | | P-value |
|---|---|---|---|
| −32.39% | −38.96% | −25.82% | 0.0006 |

TABLE 10

Odds ratio for the effect of MCI (log-transformed) in differentiating between ischemia and no-ischemia with level of significance 95% confidence interval

| Odds Ratio | 95% Wald Confidence Limits | | P-value |
|---|---|---|---|
| 0.225 | 0.084 | 0.606 | 0.0031 |

In conclusion, both PEA and MCI are significantly lower during ischemia than before ischemia is induced. Mean % reduction in PEA 24% (SD=14.08%). Mean % reduction in MCI 32.4% (SD=16.6%). PEA mean % decrease has been found to be statistically significantly greater than 10%. MCI mean % decrease has been found to be statistically significantly greater than 20%. Statistically significant odds ratios for the detection of ischemia were found for both PEA and MCI with lower values indicating a higher risk of ischemia. AUC's were approximately 0.7 for both. It is concluded that PEA and MCI show potential as diagnostic measures for the detection of ischemia and for diagnostic activities relating thereto.

Figure 4:
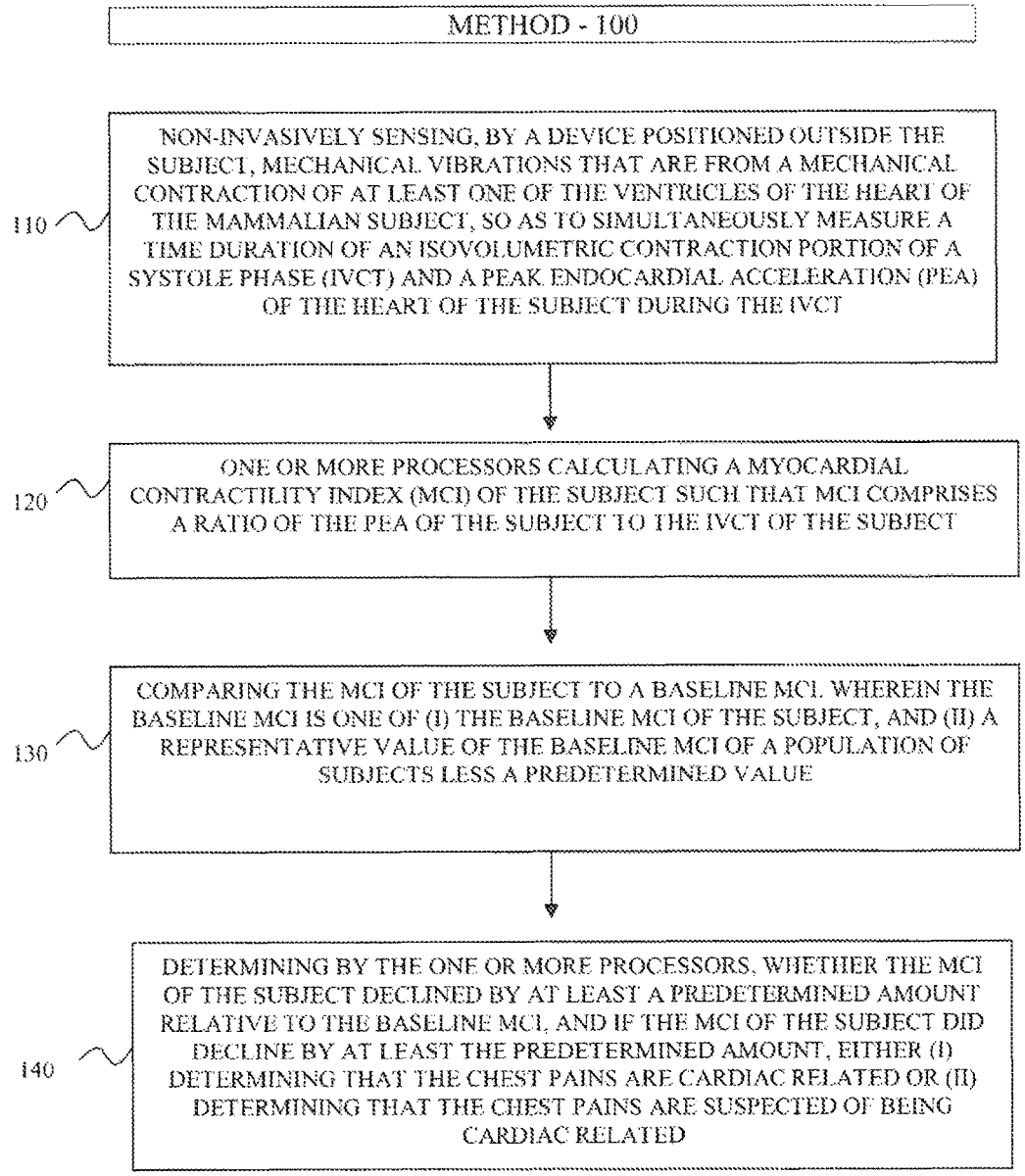
FIG. 4 is a flow chart showing a method, in accordance with one embodiment of the invention.

As seen from FIG. 4, one embodiment of the invention is a method 100 of non-invasively differentiating diagnostically between chest pain that is cardiac related and chest pain that is not cardiac related, in a mammalian subject that has a heart, the heart including ventricles. Method 100, in one embodiment, has a step 110 of non-invasively sensing, for example by a device positioned outside the subject, mechanical vibrations that are from a mechanical contraction of for example at least one of the ventricles of the heart of the mammalian subject, so as to simultaneously measure (a) IVCT, wherein in certain embodiments IVCT is a time duration of an isovolumetric contraction portion of a systole phase of a cardiac cycle of the subject; and (b) a peak endocardial acceleration (PEA) of the heart of the subject for example during the IVCT. In any embodiment, a device positioned outside the subject includes devices positioned adjacent the chest or other part of the body of the subject.

Method 100, in certain embodiments, has a further step 120 of calculating, for example dynamically and for example by one or more processors programmed by suitable software, such as special purpose software stored on memory of a computer system, a myocardial contractility index (MCI) of the subject such that the MCI comprises a ratio of the PEA of the subject to the IVCT of the subject. In some embodiments the ratio is MCI=k·PEA/IVCT, where k is a constant. In certain embodiments, k=1, such that the ratio is MCI=PEA/IVCT. The step of calculating MCI in some embodiments is done dynamically such that as the mechanical vibrations that are from a mechanical contraction of at least one of the ventricles are sensed and measured, and as the amplitudes of the waveforms for the PEA are being measured the one or more processors are dynamically calculating the MCI. In other embodiments, the MCI is calculated at select junctures of method 100 after the corresponding PEA is measured.

Method 100, in certain embodiments, has a further step 130 of comparing the MCI of the subject to a baseline MCI, wherein the baseline MCI is one of (i) the baseline MCI of the subject, and (ii) a representative value of the baseline MCI of a population of subjects less a predetermined value. In one example, the predetermined value is a predetermined number of standard deviations from a mean normal value of the baseline MCI of the population of subjects, which for example is a population of subjects other than the subject. For example, for a patient/subject that is being treated in an emergency room for chest pain, one typically would not have a baseline for that subject. In that case, one uses, in some embodiments, a baseline of a population of subjects. Assume, in one non-limiting example, that a population of subjects has a range of values exhibiting a normal distribution whose representative value (for example a mean, median, average or other representative value) is 20,000 g and whose representative value has a standard deviation of 3,000 g. Assume further in that example that two standard deviations is the predetermined value. In this example, then, one takes the mean normal value (which is the representative value) of the baseline MCI of the population of subjects, which is 20,000 g, and subtracts 6,000 g (the predetermined value) to yield 14,000 g as the baseline MCI. The comparing step 130 is performed by the one or more processors which are configured or programmed by software, for example special purpose software that in some embodiments is stored on memory.

Method 100, in certain embodiments, has a further step 140 of determining, for example by the one or more processors programmed by software stored on memory, for example special purpose software, whether the MCI of the subject declined by at least a predetermined amount relative to the baseline MCI, and if the MCI of the subject did decline by at least the predetermined amount, either (i) determining that the chest pains are cardiac related or (ii) determining that the chest pains are suspected of being cardiac related. In certain embodiments, the predetermined amount is between one tenth and three-tenth, for example one-fifth and step 140, or a step subsequent to step 140, is determining whether the MCI of the subject declined by at least one-fifth relative to the baseline MCI. In the illustrative example above, that would be 20% less than 14,000 or 11,200 g. In some embodiments the predetermined amount of MCI decline for determining that there is a suspicion that the chest pain is cardiac related is at least a certain fraction of the baseline MCI, wherein that certain fraction is 10% or 15% or 16% or 17% or 18% or 19% or 20% or 21% or 22% or 23% or 24% or 25% or 26% or 30% or any range of percentages whose lower and upper limits are any of these numbers. These numbers are only examples and other numbers or fractions or absolute amounts may apply instead.

The significance of the quantitative decline in MCI in this method 100 and likewise the significance of quantitative declines in MCI and/or in PEA in other methods and apparatuses of the invention (described below) as indicators of the fact (or in other cases of the suspicion) that chest pain is cardiac related is that Applicant's experiments show that the quantitative decline in MCI or PEA occurs due to the occlusion and continues as long as the occlusion continues, whereas it is known that in non-cardiac chest pain the MCI and PEA remain the same or even increases.

In some embodiments there is a further step of outputting an alert that the chest pain is suspected of being cardiac related, i.e. ischemia. For example, if the MCI of the subject declined by one-fifth of the baseline MCI or by more than that, in the above case a reading of 11,200 g or less, in some embodiments, there would be a further step of outputting an alert that there is a suspicion that the chest pain is cardiac related.

In some embodiments method 100 includes a step, for example a step that is part of that is subsequent to step 140, comprised of outputting an alert indicated that the chest pain is cardiac related. In certain embodiments this is based on a greater decline than would be needed to determine a mere suspicion, since for example this to determine that the chest pain is cardiac related (or is definitely cardiac related). For example, in certain embodiments, step 140 is determining whether the MCI of the subject declined by at least a predetermined of between three-tenths and one half, for example two-fifths, relative to the baseline MCI such that it is determined that the subject's chest pain is cardiac related, or is definitely cardiac related. In some embodiments the predetermined amount of MCI decline for determining that the chest pain is or is definitely cardiac related, is at least a certain fraction of the baseline MCI, wherein that certain fraction is 30% or 35% or 37% or 38% or 39% or 40% or 41% or 44% or 45% or 50% or any range of percentages whose lower and upper limits are any of these numbers. These numbers are only examples and other numbers or fractions or absolute amounts may apply instead.

In the present patent application, when "a predetermined amount" is referred to, both a relative amount qualifies as the "predetermined amount" and an absolute amount qualifies as the "predetermined amount". An example of a relative amount is a fraction or a percentage.

Figure 5:
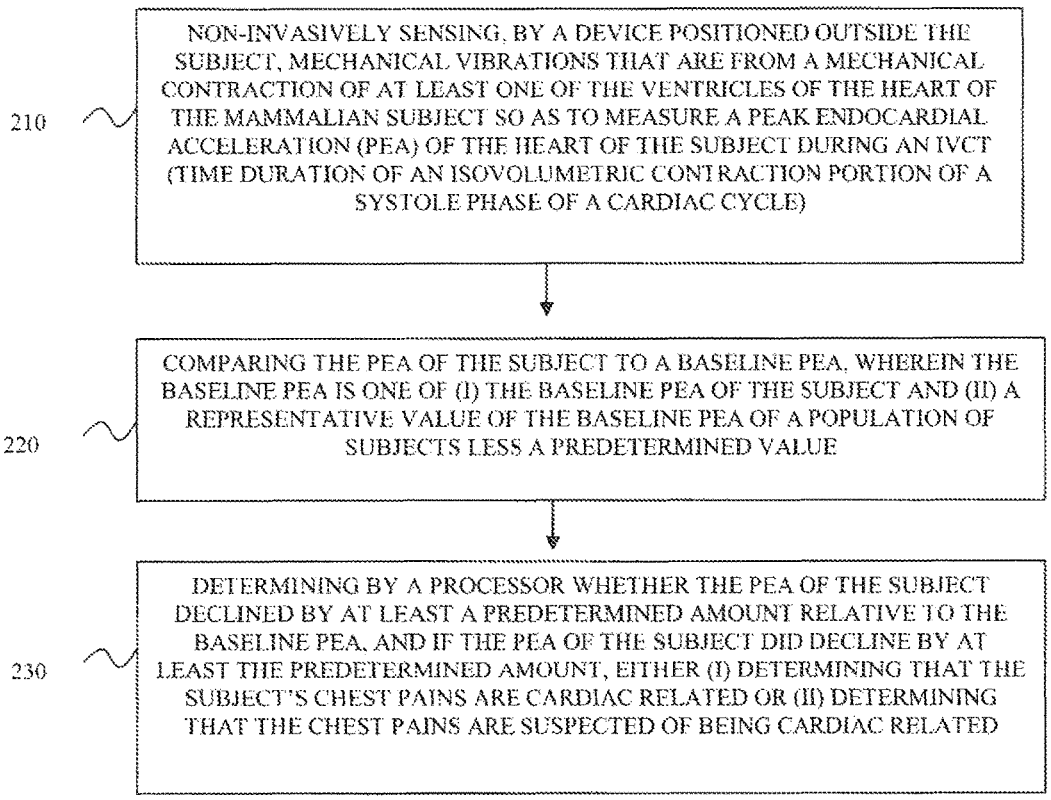
FIG. 5 is a flow chart showing a further method, in accordance with one embodiment of the invention.

As seen from FIG. 5, one embodiment of the invention is a method 200 of non-invasively differentiating diagnostically between chest pain that is cardiac related and chest pain that is not cardiac related, in a mammalian subject that has a heart, the heart including ventricles. This method 200 generally tracks method 100 except that when the PEA is measured the MCI is not calculated from the PEA. Accordingly, the predetermined amount is smaller in some embodiments of method 200 compared to the predetermined amount utilized in method 100 since MCI is more sensitive than PEA to blockages or occlusions of blood flow.

Method 200, in one embodiment, has a step 210 of non-invasively sensing, for example by a device positioned outside the subject, mechanical vibrations that are from a mechanical contraction of for example at least one of the ventricles of the heart of the mammalian subject, so as to measure a peak endocardial acceleration (PEA) of the heart of the subject for example during an IVCT, wherein IVCT is in some embodiments a time duration of an isovolumetric contraction portion of a systole phase of a cardiac cycle of the subject.

Method 200 has, in certain embodiments, a step 220 of comparing the PEA of the subject to a baseline PEA, wherein the baseline PEA is (i) the baseline PEA of the subject or (ii) a representative value of the baseline PEA of a population of subjects less a predetermined value. In some embodiments the population of subjects is a population of subjects other than the subject. The manner of selecting a representative value and a predetermined value in method 200 is similar to that of method 100. The comparing step 130 is performed by the one or more processors programmed by software, for example special purpose software stored on memory, in some embodiments. In certain embodiments, the one or more processors obtain the PEA from digital signals that have been converted from analog signals corresponding to the sensed mechanical vibrations.

Method 200 has, in some embodiments, a step 230 of determining by a processor programmed by software stored on memory, whether the PEA of the subject declined by at least a predetermined amount relative to the baseline PEA, and if the PEA of the subject did decline by at least the predetermined amount, either (i) determining that the subject's chest pains are cardiac related or (ii) determining that the chest pains are suspected of being cardiac related. As in method 100, both a relative amount qualifies to be the "predetermined amount" and an absolute amount qualifies to be the "predetermined amount". An example of a relative amount is a fraction or a percentage.

In some embodiments, step 230 comprises determining whether the PEA of the subject declined by at least a predetermined amount, the predetermined amount being between one twentieth and one fifth, for example at least one tenth relative to the baseline PEA. Method 200 has a step, in some embodiments, of outputting an alert that there is a suspicion that the chest pain is cardiac related upon determining that the PEA of the subject declined by the predetermined amount, for example when the predetermined is one tenth or another number between one twentieth and one-fifth. In some embodiments the predetermined amount of PEA decline for determining that there is a suspicion that the chest pain is cardiac related is at least a certain fraction of the baseline MCI, wherein that certain fraction is 5% or 9% or 10% or 11% or 12% or 13% or 14% or 15% or 16% or 17% or 18% or 20% or any range of percentages whose lower and upper limits are any of these numbers. These numbers are only examples and other numbers or fractions or absolute amounts may apply instead.

In some embodiments, method 200 has a step of determining, by one or more processors programmed by software stored on memory, whether the PEA of the subject declined by at least two tenths relative to the baseline PEA, which determination would indicate that the chest pain is or definitely is cardiac related. In some embodiments the predetermined amount of PEA decline for determining that the chest pain is, or definitely is, cardiac related is at least a certain fraction of the baseline MCI, wherein that certain fraction is between one tenths and three-tenths, or for example 15% or 16% or 17% or 18% or 19% or 20% or 21% or 21% or 22% or 23% or 24% or 25% or any range of percentages whose lower and upper limits are any of these numbers. These numbers are only examples and other numbers or fractions or absolute amounts may apply instead.

In some embodiments, there is a further step in method 200 of outputting an alert that the chest pain is cardiac related.

In certain embodiments, the predetermined amount is a relatively high amount. For example, if the determination being made is not just that the chest pain is cardiac related but rather that the patient suffers from a myocardial infarction, the predetermined amount is, in certain embodiments, approximately twice as high as for determining definite cardiac related chest pains. For example, method 200 has, in certain embodiments, a step of determining myocardial infarction, for example from detecting a lack of movement of ischemic and necrotic regions of a heart, as a result of detecting a decline in MCI of at least certain fraction relative to the baseline MCI, wherein the certain fraction is between half and four-fifths, for example four-fifths.

Figure 12:
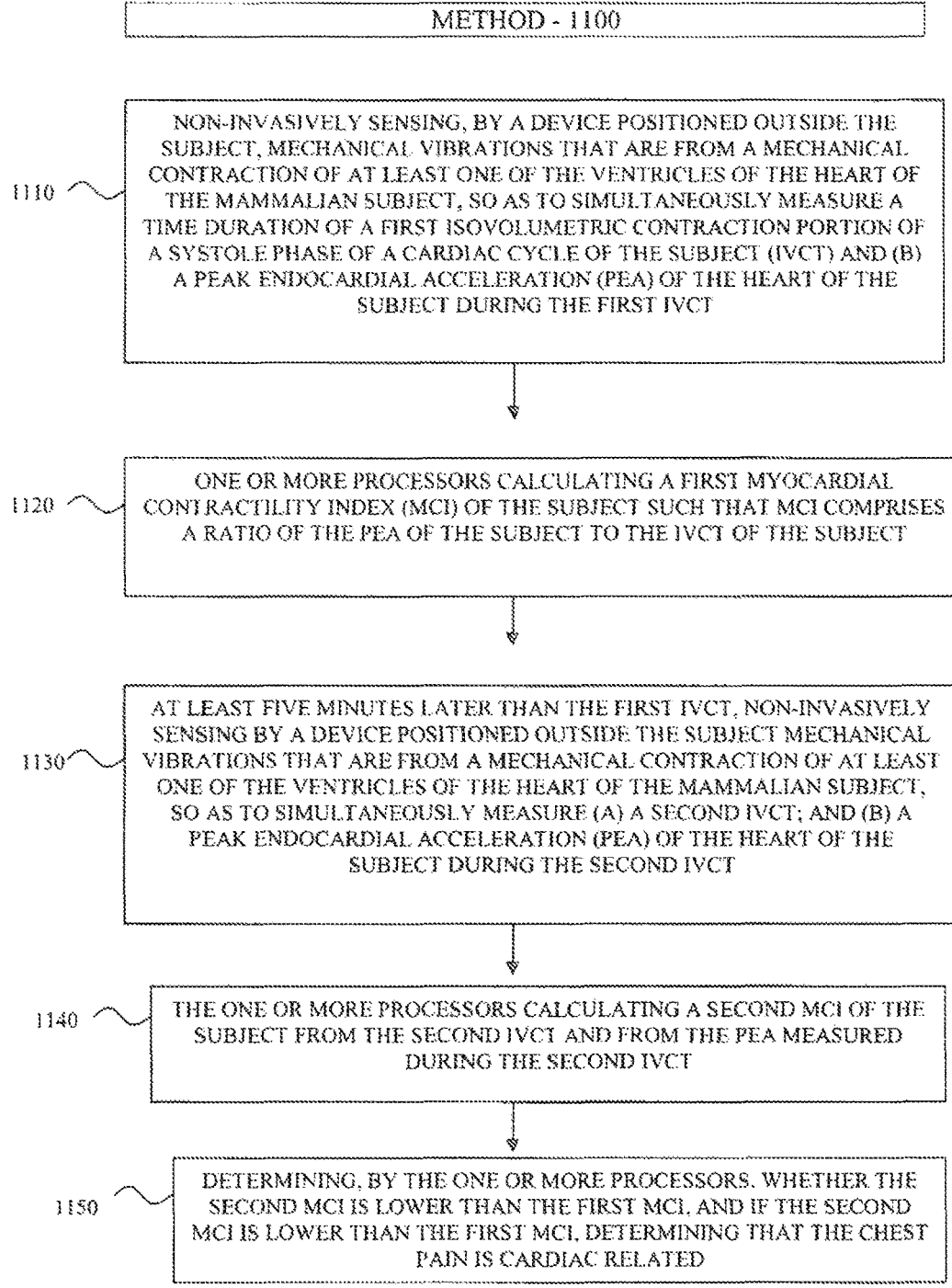
FIG. 12 is a flow chart showing a further method, in accordance with one embodiment of the invention.

As shown in FIG. 12, in a further embodiment, particularly useful for a patient at home or distant from medical personnel, the invention is a method 1100 of dynamically differentiating diagnostically, non-invasively, between chest pain that is cardiac related and chest pain that is not cardiac related, in a mammalian subject that has a heart, the heart including ventricles. Method 1100 comprises a step 1110 of non-invasively sensing, by a device positioned outside the subject, mechanical vibrations that are from a mechanical contraction of at least one of the ventricles of the heart of the mammalian subject, so as to simultaneously measure (a) a first IVCT, wherein IVCT is a time duration of an isovolumetric contraction portion of a systole phase of a cardiac cycle of the subject; and (b) a peak endocardial acceleration (PEA) of the heart of the subject during the first IVCT.

Method 1100 also comprises in some embodiments a step 1120 one or more processors of calculating a first myocardial contractility index (MCI) of the subject such that MCI comprises a ratio of the PEA of the subject to the IVCT of the subject. In some embodiments the ratio is MCI=k·PEA/IVCT, where k is a constant. In one such embodiment, k=1, such that the ratio is MCI=PEA/IVCT. The one or more processors, programmed by special purpose software stored on memory, in some embodiments, calculates the first MCI from digital signals that derive from analog signals corresponding to the mechanical vibrations sensed during the second period. Suitable hardware and software are included, in certain embodiments, to transmit and/or convert to digital form the data from the mechanical vibrations to the one or more processors for processing. This is the case for any method of the invention.

Method 1100 also comprises in certain embodiments a further step 1130 of a predetermined length of time later, for example five minutes later, ten minutes later, or a different number of minutes between 5 minutes and 10 minutes later, than the first IVCT, non-invasively sensing by a device positioned outside the subject mechanical vibrations that are from a mechanical contraction of at least one of the ventricles of the heart of the mammalian subject, so as to simultaneously measure (a) a second IVCT; and (b) a peak endocardial acceleration (PEA) of the heart of the subject during the second IVCT. The examples of 5 minutes and 10 minutes are non-limiting examples. Other suitable examples of time intervals are usable in some embodiments such as 1, 3, 11, 13, 15, 17, 18, 20, 25 or 30 minutes or a different number of minutes, where this different number is between 1 and 30 minutes, or at least such a number of minutes or another suitable time interval.

In a step 1140 in some embodiments of method 1100, the one or more processors calculate a second MCI of the subject, for example from the second IVCT and from the PEA measured during the second IVCT. Method 1100 includes a step in certain embodiments of comparing the second MCI to the first MCI and determining, by the one or more processors, whether the second MCI is lower than the first MCI, and if the second MCI is lower than the first MCI determining that the chest pain is cardiac related. The operating assumption is that whereas the MCI (and PEA) remains the same or increases in the case of non-cardiac related chest pain, the MCI (or PEA) declines over time in the case of cardiac related chest pain (until a certain point at which the decline has concluded). In some cases, the determining is determining whether the second MCI is lower than the first MCI by at least a predetermined amount. This amount is between zero and a relatively small amount in some embodiments.

In some embodiments of method 1100 further verification of the decline is obtained by an additional step of continuing the dynamic measurements of MCI by, beginning a predetermined length of time later, for example five minutes later, ten minutes later, or a different number of minutes between 5 minutes and 10 minutes later, or a different number of minutes between one and thirty minutes later, than the second IVCT, non-invasively sensing by a device positioned outside the subject mechanical vibrations that are from a mechanical contraction of at least one of the ventricles of the heart of the mammalian subject, so as to simultaneously measure (a) a third IVCT; and (b) a peak endocardial acceleration (PEA) of the heart of the subject during the third IVCT, the one or more processors then calculating a third MCI of the subject from the third IVCT and from the PEA measured during the third IVCT, comparing the third MCI to the second MCI (or to the baseline MCI) and determining, by the one or more processors whether the third MCI is lower than the second MCI and if the third MCI is lower than the second MCI, determining at a higher degree of certainty, that the chest pain is cardiac related so as to verify an earlier determination that the chest pain is cardiac related (the earlier determination being based on the earlier comparison between the first MCI and the second MCI), or else in other embodiments simply determining that the chest pain is cardiac related, if for example one prefers to not rely on the earlier decline from the first MCI to the second MCI.

Figure 13:
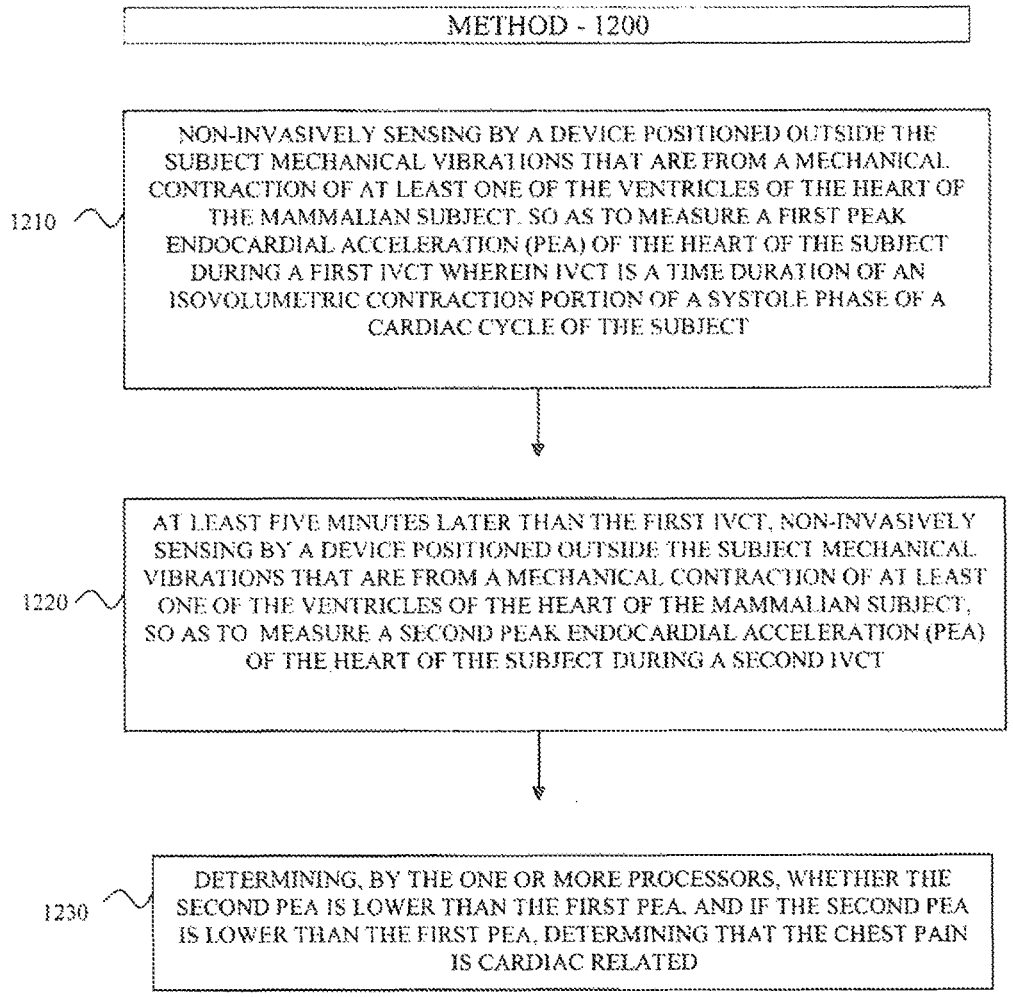
FIG. 13 is a flow chart showing a further method, in accordance with one embodiment of the invention.
Figure 15:
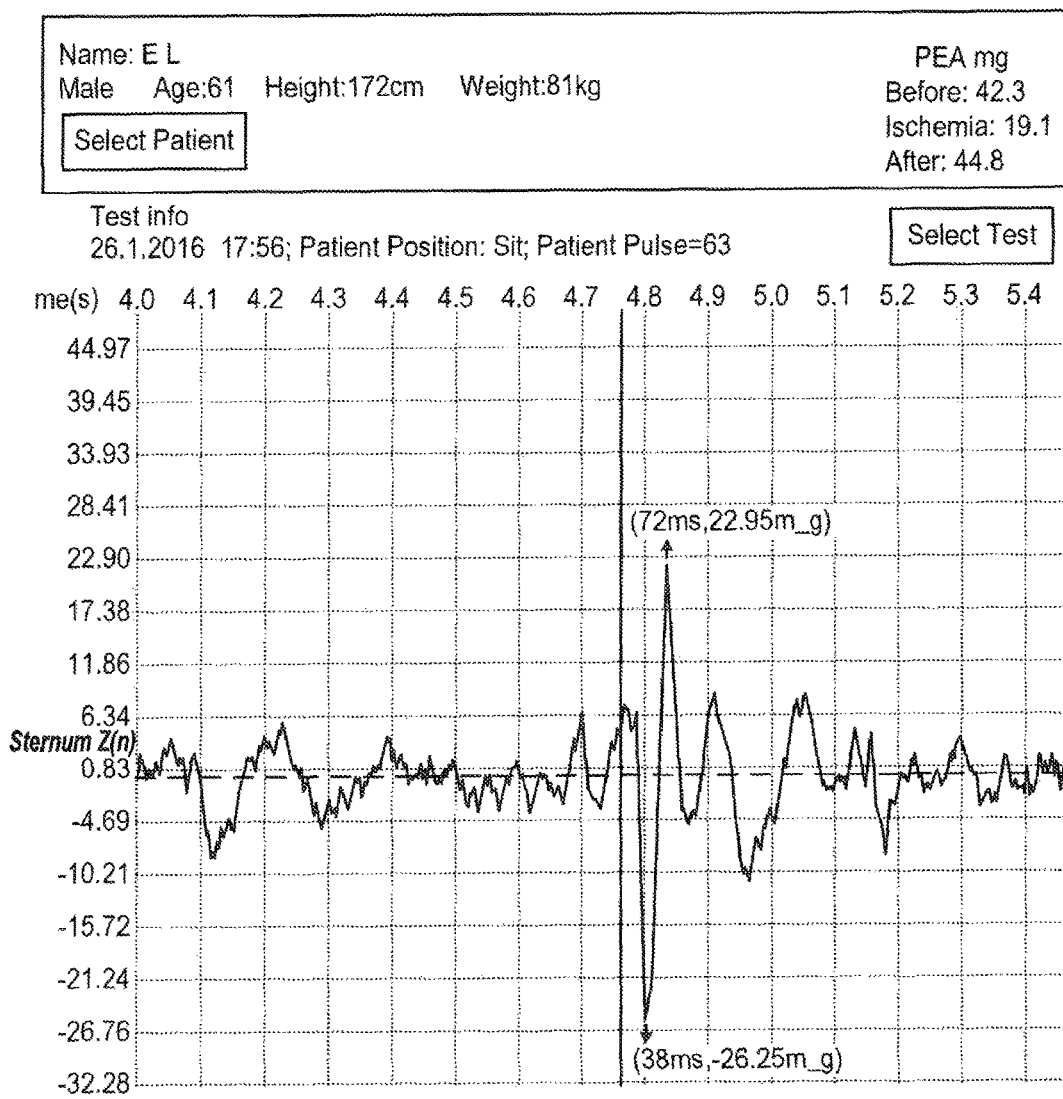
FIG. 15 is a graph of an analog signal of mechanical vibrations from the mechanical contraction of at least one ventricle obtained by a sensor unit, in accordance with one embodiment of the invention.
Figure 16:
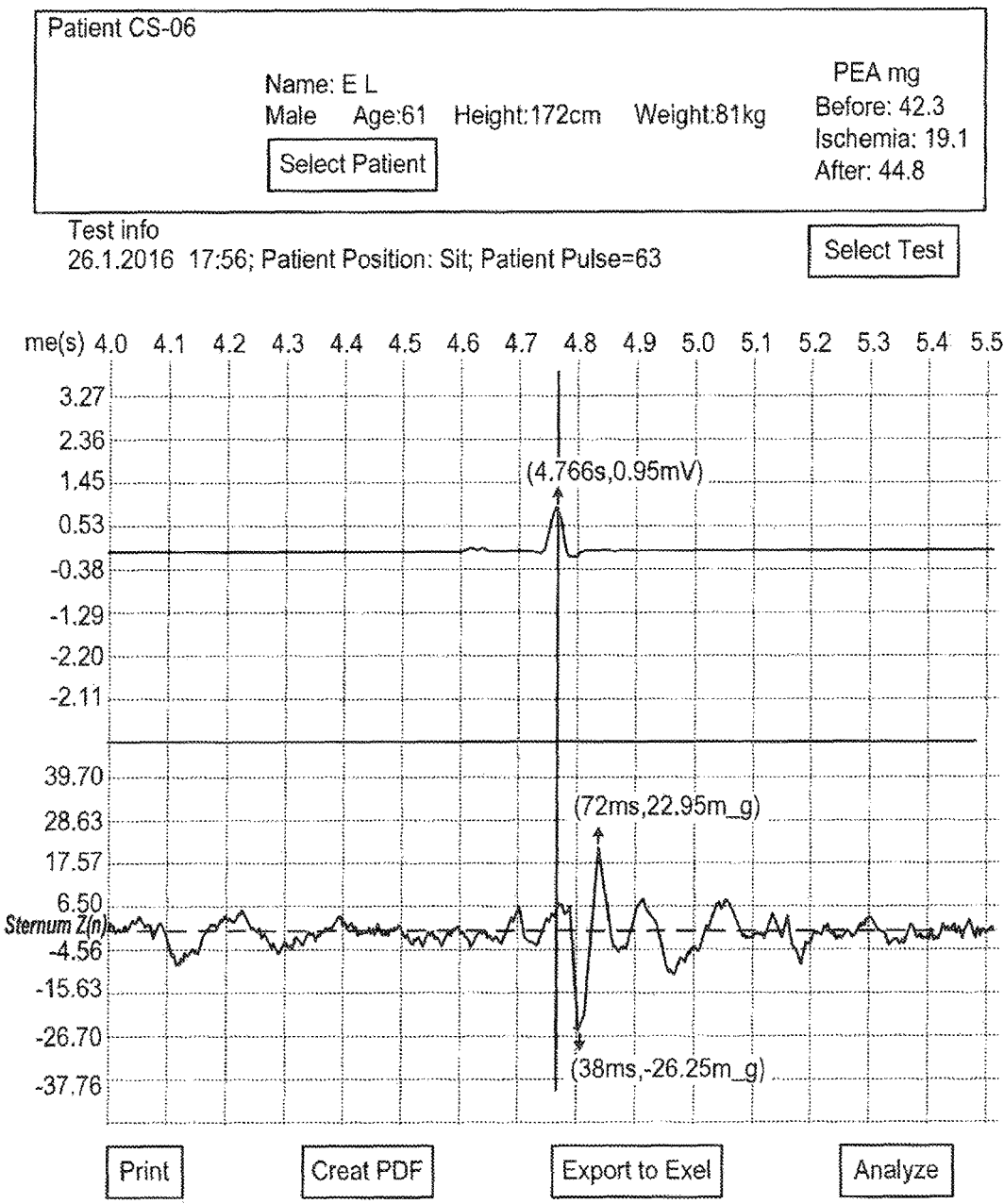
FIG. 16 is a graph of two analog signals of a single patient obtained by a sensor unit, including an ECG signal and an analog signal of mechanical vibrations from the mechanical contraction of at least one ventricle, in accordance with one embodiment of the invention.

As shown in FIG. 13, the invention, in a further embodiment, is a method 1200 of dynamically differentiating diagnostically, non-invasively, between chest pain that is cardiac related and chest pain that is not cardiac related, in a mammalian subject that has a heart, the heart including ventricles. Method 1200 has a step 1210 in some embodiments of non-invasively sensing by a device positioned outside the subject mechanical vibrations that are from a mechanical contraction of at least one of the ventricles of the heart of the mammalian subject, so as to measure a first peak endocardial acceleration (PEA) of the heart of the subject during a first IVCT wherein IVCT is a time duration of an isovolumetric contraction portion of a systole phase of a cardiac cycle of the subject.

Method 1200 has a step 1220 in some embodiments of, beginning a predetermined length of time later, for example five minutes later, ten minutes later, or a different number of minutes between 5 minutes and 10 minutes later, or between 1 and 30 minutes later, than the first IVCT, non-invasively sensing by a device positioned outside the subject mechanical vibrations that are from a mechanical contraction of at least one of the ventricles of the heart of the mammalian subject, so as to measure a second peak endocardial acceleration (PEA) of the heart of the subject during a second IVCT.

Method 1200 has a step 1230 in some embodiments of comparing the second PEA to the first PEA and determining by one or more processors whether the second PEA is lower than the first PEA, and if the second PEA is lower than the first PEA determining that the chest pain is cardiac related. In some cases, the determining is determining whether the second PEA is lower than the first PEA by at least a predetermined amount. This amount is between zero and a relatively small amount in some embodiments. An output unit outputs an alert of the determination in some embodiments.

In some embodiments of method 1200 further verification of the decline is obtained by an additional step of continuing the dynamic measurements of PEA by, during a third sensing period beginning a predetermined length of time later, for example five minutes later, ten minutes later, or a different number of minutes between 5 minutes and 10 minutes later or between 1 and 30 minutes later, than the second sensing period (as measured in some embodiments by being later than an end of the second sensing period) non-invasively sensing by a device positioned outside the subject mechanical vibrations that are from a mechanical contraction of at least one of the ventricles of the heart of the mammalian subject so as to measure a third PEA of the heart of the subject during an IVCT of the subject and comparing the third PEA to the second PEA (or to the baseline PEA) and determining whether the third PEA is lower than the second PEA, and if the third PEA is lower than the second PEA, further verifying that the chest pain is cardiac related, or in other embodiments determining that the chest pain is cardiac related if for example one prefers to not rely on the earlier decline from the first MCI to the second MCI. An output unit outputs an alert of the determination in some embodiments.

Methods 1100 and 1200 for dynamically differentiating diagnostically, non-invasively, between chest pain that is cardiac related and chest pain that is not cardiac related provide very strong indications of ischemia (cardiac-related chest pain) since the decline (of MCI or PEA) is shown to continue to decline dynamically.

Figure 3B:
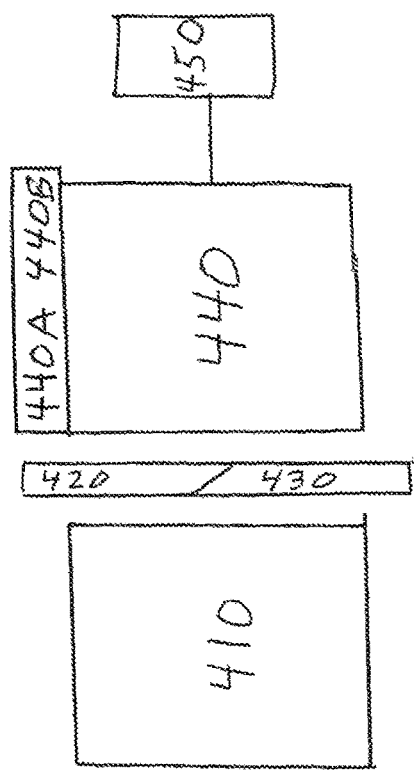
FIG. 3B is a schematic view of an apparatus, in accordance with one embodiment of the invention.
Figure 3A:
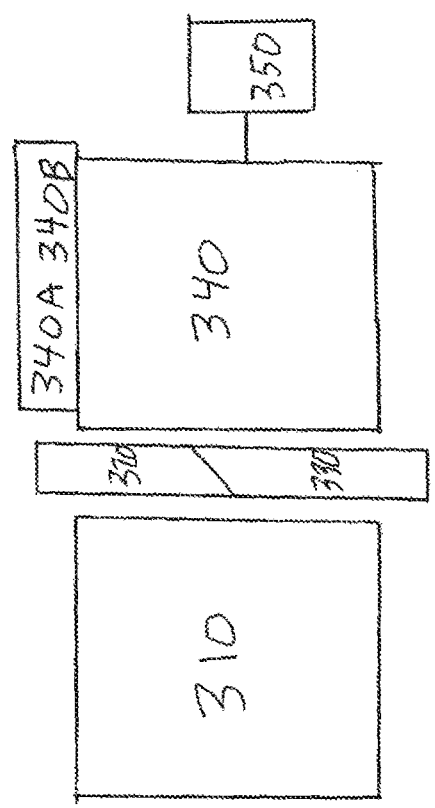
FIG. 3A is a schematic view of an apparatus, which apparatus is configured to utilize MCI, a new parameter, in accordance with one embodiment of the invention.

In one embodiment shown in FIG. 3A, the invention is an apparatus 300 configured to non-invasively medically diagnose whether chest pain is cardiac related or not, i.e. to differentiate diagnostically between chest pain that is cardiac related and chest pain that is not cardiac related, in a mammalian subject that has a heart, the heart including ventricles. The apparatus 300 in some embodiments comprises a sensor unit 310, which in some embodiments comprises a measurement device such as an accelerometer unit 310 configured to non-invasively sense, by the device for example positioned outside the subject, mechanical vibrations that are from a mechanical contraction of at least one of the ventricles of the heart of the mammalian subject so as to simultaneously measure (a) IVCT, wherein IVCT is a time duration of an isovolumetric contraction portion for example of a systole phase of a cardiac cycle of the subject, and (b) a peak endocardial acceleration (PEA) of the heart of the subject during the IVCT. The accelerometer unit 310 is adapted to be attached to a patient such as at the patient's chest, for example using a belt, in some embodiments.

Figure 3C:
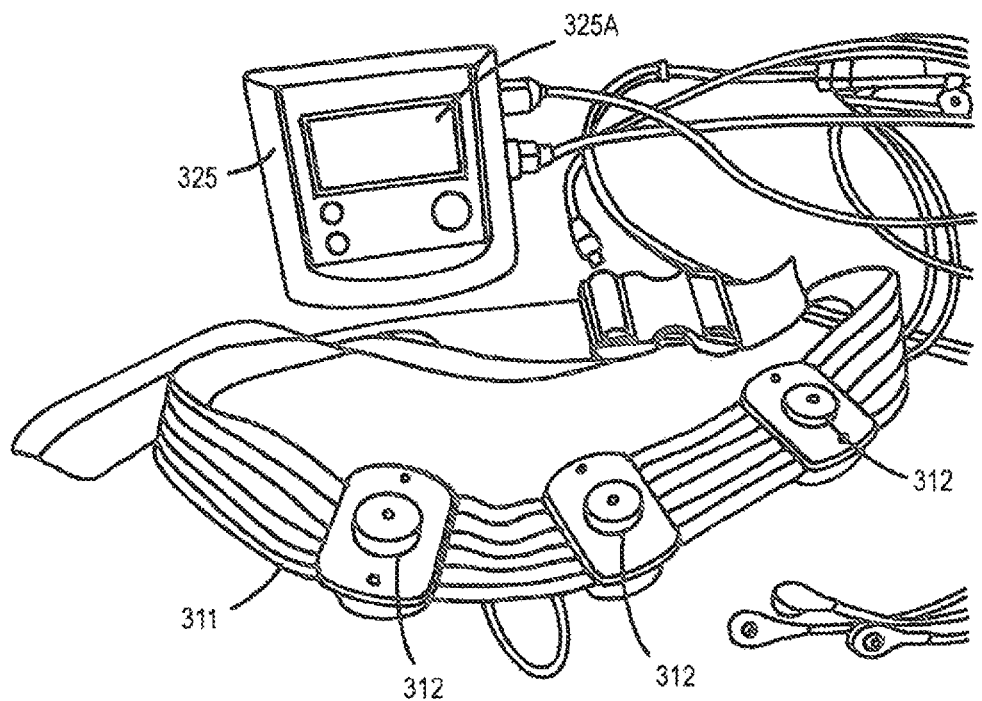
FIG. 3C is a perspective view showing a sensor unit and an operation unit of an apparatus, which apparatus is configured to utilize MCI, a new parameter, in accordance with one embodiment of the invention.
Figure 3D:
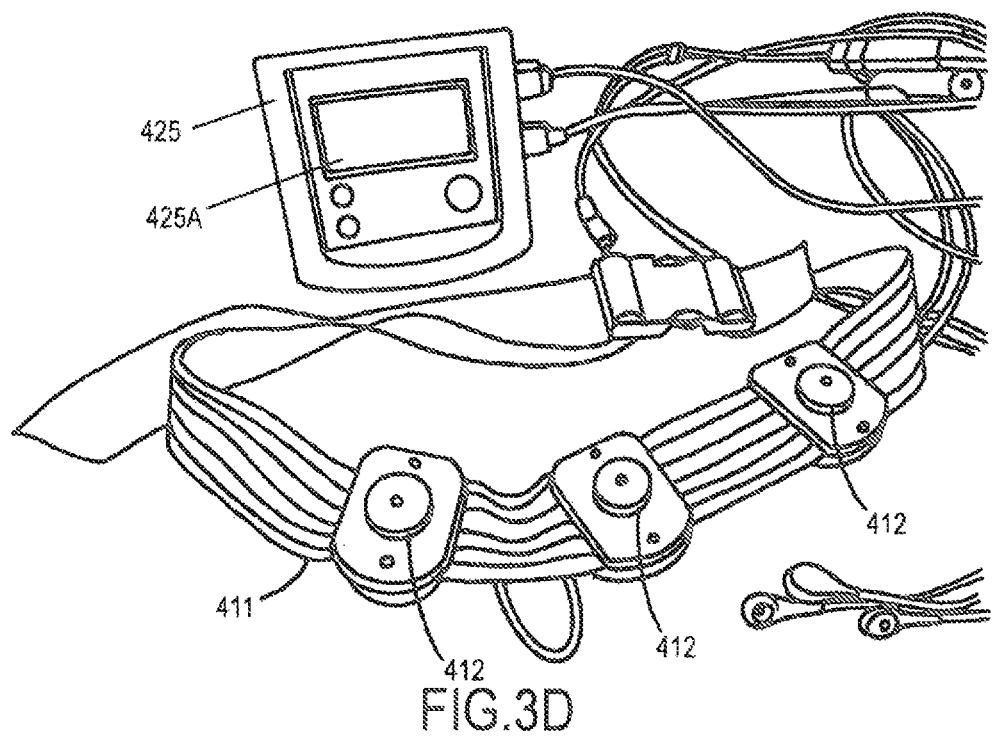
FIG. 3D is a perspective view showing a sensor unit and an operation unit of an apparatus, in accordance with one embodiment of the invention.
Figure 17:
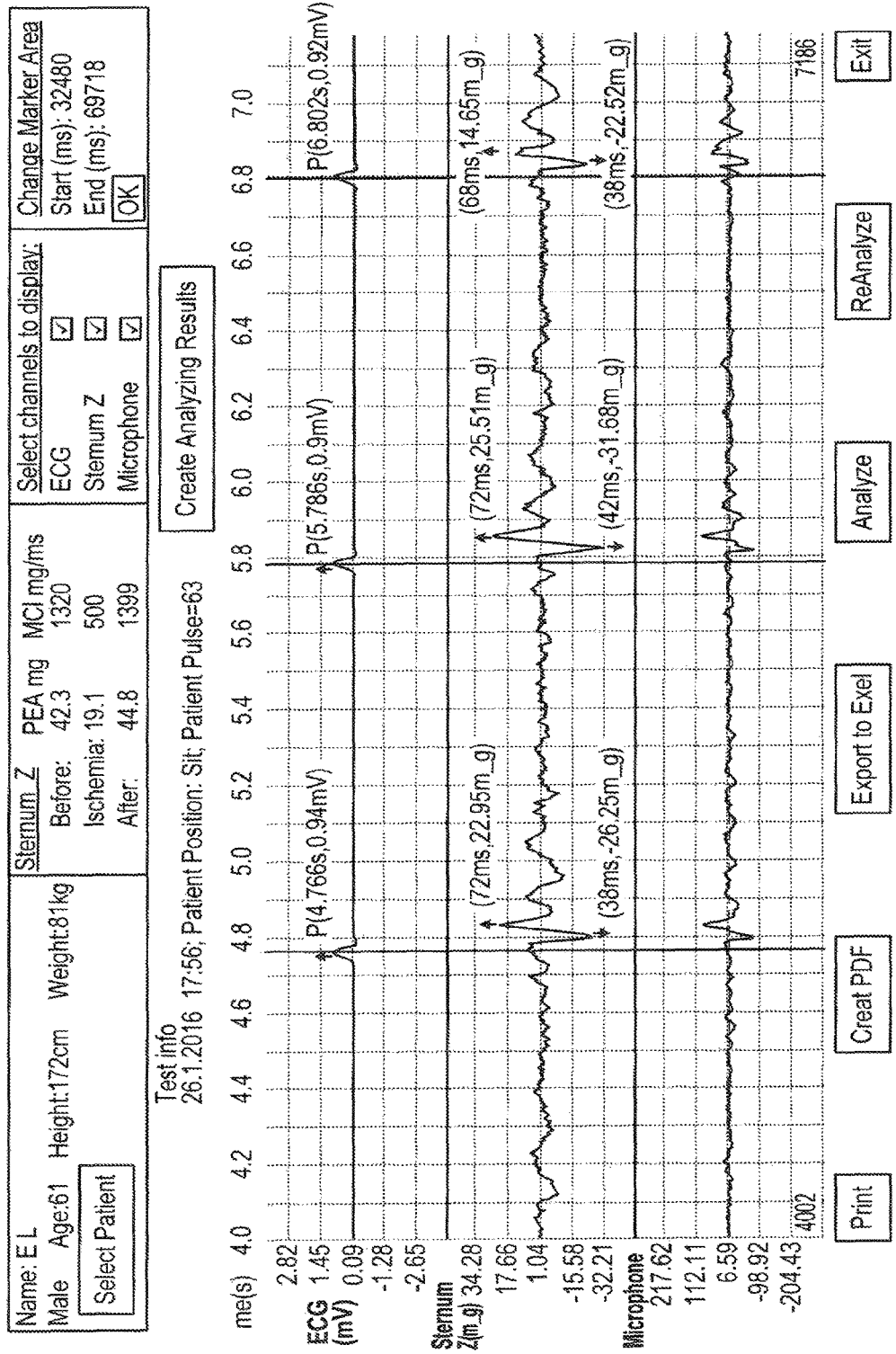
FIG. 17 is a graph showing three analog signals of a single patient obtained by a sensor unit, wherein the top signal is an ECG signal, the bottom signal is a microphone signal and the middle signal is of mechanical vibrations from the mechanical contraction of at least one ventricle of the patient, in accordance with one embodiment of the invention.

The sensor unit 310 comprises in some embodiments an accelerometer, a microphone, straps and ECG electrodes. The purpose of the ECG electrodes is to identify appearance of the R peak of the QRS complex, which corresponds roughly to the opening of the isovolumetric contraction, whose time duration is represented by IVCT. FIG. 3C shows a non-limiting example of a sensor unit 310 usable for apparatus 300. FIG. 3D shows a non-limiting example of a sensor unit 410 usable for apparatus 400. FIG. 17 is a graph of an analog signal obtain by a sensor unit (310, 410), in accordance with one embodiment of the invention. FIG. 18 is a graph showing three signals, the top being an ECG signal, the bottom being a microphone signal and the middle signal being an analog signal obtained by a sensor unit, in accordance with one embodiment of the invention. From the graph of FIG. 17 and from the signal in the middle of FIG. 18, one computes the PEA, for example using techniques known in the medical literature. From the PEA and the IVCT, one or more processors execute software to compute the MCI. In some embodiments MCI=k·PEA/IVCT, where k is a constant. In one such embodiment, k=1, such that MCI=PEA/IVCT. The ECG signal is used to determine the location of the IVCT from the graph.

Apparatus 300 includes, in some embodiments, hardware 320 and software 330 configured to convert the sensed mechanical vibrations into digital signals corresponding to the PEA and IVCT and usable by digital processors. Examples of such hardware and software include signal conditioning circuitry and analog to digital converters. Apparatus 300 includes in general in some embodiments any suitable hardware and software for transmitting data or a signal(s) corresponding to the sensed mechanical vibrations, and/or converting to digital form this data or signal(s) corresponding to the sensed mechanical vibrations, to the one or more processors 340 for use, processing, etc. The hardware 320 and software 330 in some embodiments (see FIG. 3) is separate from the sensor unit 310 and from the one or more processors 340. In other embodiments the hardware 320 and/or software 330 is part of one or more of the sensor unit 310 and the one or more processors 340.

Apparatus 300 also includes in some embodiments one or more processors 340, programmed by special purpose software 340A that in some embodiments is stored on a memory 340B. The one or more processors 340 are part of or comprise in some embodiments a determination unit 344. The determination unit 344 is a computer system in some embodiments. The one or more processors or the determination unit is configured to receive digital signals corresponding to the sensed mechanical vibrations and to calculate, for example dynamically, an MCI of the subject. MCI is a myocardial contractility index that comprises a ratio of the PEA of the subject to the IVCT of the subject. The one or more processors 340 (or determination unit) are configured to receive the signals from the sensor unit 310 either through a wired connection or wirelessly.

The one or more processors are in some embodiments configured by software to compare the MCI of the subject to a baseline MCI, wherein the baseline MCI is one of (i) the baseline MCI of the subject, and (ii) a representative value of the baseline MCI of a population of subjects less a predetermined value, i.e. a predetermined number of standard deviations from the representative value (the representative value being for example a mean, median, average or representative value), for example the mean normal value, of the baseline MCI of a population of subjects. The manner of selecting the representative value and the predetermined value for apparatus 300 (and for apparatus 400) is similar to that described in connection with methods 100, 200. The one or more processors are in some embodiments configured by software to determine whether the MCI of the subject declined during the sensing period by at least a predetermined amount relative to the baseline MCI.

The at least the predetermined amount (relative to the baseline MCI) is at least one-fifth in some embodiments, for example when the determination is whether or not there is a suspicion that the chest pain is cardiac related. In some embodiments, the at least a predetermined amount is at least a certain fraction of the baseline MCI, wherein that certain fraction is 15% or 16% or 17% or 18% or 19% or 20% or 21% or 21% or 22% or 23% or 24% or 25% or any range of percentages whose lower and upper limits are any of these numbers. These numbers are only examples and other numbers or fractions or absolute amounts may apply instead.

In some embodiments, an output unit outputs an alert that there is a suspicion that the chest pain is cardiac related when at least the predetermined amount has been reached. In some embodiments, the predetermined amount is a certain fraction wherein the certain fraction of the baseline MCI is two-fifths, for example when the determination is whether or not the patient's chest pain is cardiac related or not, or is definitely cardiac related or not. Instead of two-fifths, the predetermined amount in some embodiments is a fraction of the baseline MCI between three-tenths and one half, or 52%, 56%, or 60% or any range of percentages whose lower and upper limits are any of these numbers. These numbers are only examples and other numbers or fractions or absolute amounts may apply instead.

Apparatus 300 in some embodiments includes an output unit 350 that outputs an alert that the chest pain is cardiac related when at least the predetermined amount of decline is reached. Output unit 350 and one or more processors 340 are part of the same computer system in some embodiments and in other embodiments they are not part of a same computer system.

As shown in FIG. 3B, the invention, in one embodiment, is an apparatus 400 (or system 400) configured to non-invasively medically diagnose whether chest pain is cardiac related or not, i.e. to differentiate diagnostically between chest pain that is cardiac related and chest pain that is not cardiac related, in a mammalian subject that has a heart, the heart including ventricles. Apparatus 400 comprises in some embodiments a sensor unit 410, which in some embodiments comprises a measurement device such as an accelerometer unit 410 configured to non-invasively sense, by the device positioned outside the subject, mechanical vibrations that are from a mechanical contraction of at least one of the ventricles of the heart of the mammalian subject so as to measure a peak endocardial acceleration (PEA) of the heart of the subject during an IVCT, wherein IVCT is a time duration of an isovolumetric contraction portion of a systole phase of a cardiac cycle of the subject. The accelerometer unit 410 is adapted to be attached to a patient such as at the patient's chest, for example using a belt, in some embodiments.

Apparatus 400 includes, in some embodiments, hardware 420 and software 430 configured to convert the sensed mechanical vibrations into digital signals corresponding to the PEA. An example of such hardware and software is an analog to digital converter. Apparatus 400 includes, in some embodiments any suitable hardware and software for transmitting the sensed mechanical vibrations to one or more processors 440. Furthermore, any of the methods of the invention have, in some embodiments, such suitable hardware and software for transmitting, and/or converting to digital form, data or a signal(s) corresponding to the sensed mechanical vibrations to the one or more processors 440 for use, processing, analysis, etc. The hardware 420 and software 430 in some embodiments (see FIG. 3) is separate from the sensor unit 410 and from the one or more processors 440. In other embodiments the hardware 420 and/or software 430 is part of one or more of the sensor unit 410 and the one or more processors 440.

Apparatus 400 includes in some embodiments one or more processors 440 programmed by special purpose software 440A that in some embodiments is stored on a memory 440B. The one or more digital processors are part of a determination unit 444 in some embodiments. In some embodiment the determination unit 444 is a computer system. The one or more processors or the determination unit is configured to receive digital signals corresponding to the sensed mechanical vibrations, to compare the digital signals that correspond to the PEA of the subject to a baseline PEA, wherein the baseline PEA is one of (i) the baseline PEA of the subject and (ii) a representative value (for example a mean normal value) of the baseline PEA of a population of subjects less a predetermined value, i.e. a predetermined number of standard deviations from the representative value (the representative value being for example a mean, median, average or other representative value), and to determine whether chest pain of the subject is cardiac related or not cardiac related based on whether the PEA of the subject declined during the sensing period by at least a predetermined amount relative to the baseline PEA. The one or more processors 440 (or determination unit) are configured to receive the signals from the sensor unit 410 either through a wired connection or wirelessly.

The one or more processors 440 are configured by software 440A stored on memory 440B in some embodiments to determine whether there is merely a suspicion that the chest pain is ischemia. Especially (although not necessarily only) in such cases, the predetermined amount is one tenth such that if the decline is at least one tenth relative to the baseline PEA there is such a suspicion. Instead of one-tenth, the predetermined amount, in some embodiments is a certain fraction of the baseline PEA, for example between one twentieth and one fifth, or wherein that certain fraction is 9% or 10% or 11% or 12% or 13% or 14% or 15% or 16% or 17% or 18% or any range of percentages whose lower and upper limits are any of these numbers. These numbers are only examples and other numbers or fractions or absolute amounts may apply instead.

An output unit 450 in some embodiments outputs an alert. For example, output unit 450 outputs that there is a suspicion that the chest pain is cardiac related, i.e. ischemia, in some embodiments, when the selected predetermined amount is reached. The one or more processors 440 are configured by software in some embodiments to determine whether the chest pain is ischemia or is definitely ischemia. In such cases, although not necessarily only in such case, the predetermined amount is two tenths such that if the decline is at least two tenths relative to the baseline PEA, the chest pain is determined to be ischemia. Instead of two-tenths, in some embodiments the predetermined amount relative to the baseline PEA is a certain fraction of the baseline PEA, for example between one tenth and three-tenths, or wherein that certain fraction is 15% or 20% or 22% or 24% or 26% or 28% or any range of percentages whose lower and upper limits are any of these numbers. These numbers are only examples and other numbers or fractions or absolute amounts may apply instead.

An output unit 450 of apparatus 400 outputs an alert that the chest pain is cardiac related, i.e. ischemia, in some embodiments when the selected predetermined amount relative to the baseline PEA (which may be a certain fraction such as two-tenths in this case) is reached. Output unit 450 and one or more processors 440 are part of the same computer system in some embodiments and in other embodiments they are not part of a same computer system.

Output unit 350 of apparatus 300 and/or output unit 450 of apparatus 400 comprises, in some embodiments, an indicator unit in communication with the determination unit, the indicator unit configured to issue an indication of at least one of (i) whether the chest pain is cardiac related or not and (ii) whether the chest pain is suspected of being cardiac related or not.

Notwithstanding FIGS. 3A and 3B, some embodiments of apparatus 300 and/or apparatus 400 are defined so as to not include the analog to digital converter or other hardware and software configured to convert the analog signal to a digital signal.

Any apparatus of the invention may be described as a "system" if the one or more processors are remote from the measurement device and for example the one or more processors are configured to communicate to the measurement device and or associated hardware and software wirelessly and/or the sensor unit or measurement device is configured to communicate to the one or more remote processors.

Apparatus 300 and apparatus 400 are in some embodiments configured to implement the "dynamic" embodiments outlined in methods 1300 and 1400 as well as any of the other methods or embodiments of the invention.

The following paragraphs numbered (a) through (k) contain a more detailed description of one non-limiting example of how to implement an apparatus 300 or apparatus 400 and it is emphasized that the details therein are not intended to at all limit the range of possible embodiments of apparatus 300, 400 or possible ways to implement apparatus 300, 400 or methods using apparatus 300, 400.

(A) In some embodiments, apparatus 300, 400 is a non-invasive cardiac monitor configured to measure, process, store and/or display information derived in certain embodiments from a sensor such as an accelerometer (configured in certain embodiments to record vibrational waveforms produced by the heart contractions and transmitted to the chest wall) and in some embodiments also one or more of an electrocardiogram (ECG) and a microphone. Apparatus 300, 400, in some embodiments, is configured to measure the timing of part of the events in the cardiac cycle. Apparatus 300, 400 in some embodiments where the user is for example at home provides a cardiac parameter which in some embodiments indicates myocardial ischemia (or a pattern of myocardial ischemia) for further analysis by the physician, which is particularly useful for patients with suspected cardiac abnormalities away from medical personnel. In a particular embodiment, apparatus 300, 400 measures and monitors ECG signals, mechanical action of the heart by an accelerometer and the audio signals of the heart using a microphone in some embodiments. In other embodiments of the invention, apparatus 300, 400 omits one or more of (i) the ECG leads and (ii) the microphone. For example, in some embodiments apparatus 300, 400 senses and monitors signals from an accelerometer and ECG signals but does not measure or monitor audio signals of the heart from a microphone. In still other embodiments of the invention, apparatus 300, 400 does not measure and monitor ECG signals and only senses and monitors (and analyzes) vibrational waveforms produced by the heart's mechanical contractions and transmitted to the chest wall (with or without audio signals from a microphone).

(B) In certain embodiments of apparatus 300, 400, the apparatus comprises the following three main components: (i) a sensor unit 310, 410 that includes an elastic belt fitted with for example two accelerometer sensors, ECG leads and a microphone; (ii) a hand-held portable operation unit 325, 425, battery powered digitizing transceiver unit with an embedded micro-processor and (iii) dedicated software 340A,440A configured to perform data analysis and hosted on a computer such as a personal computer (PC) 340, 440 or laptop computer 340, 440 or any other appliance having within it a suitable processor and software, and also configured for control of other components.

(C) The elastic belt 311, 411 with the sensors 312, 412 is configured to be attached for example to the chest of the patient for example with the sensors adjacent the chest of the subject according to some embodiments. The sensor unit 310, 410 provides mechanical vibration correlated signals, ECG signals and audio signals but in other embodiments provides additional signals (i.e. from additional sensors) and in still other embodiments provides fewer signals (i.e. from fewer sensors). The dedicated software hosted by the PC analyzes the recorded waveform and measures a timing of parts of the events in the cardiac cycle.

Figure 3E:
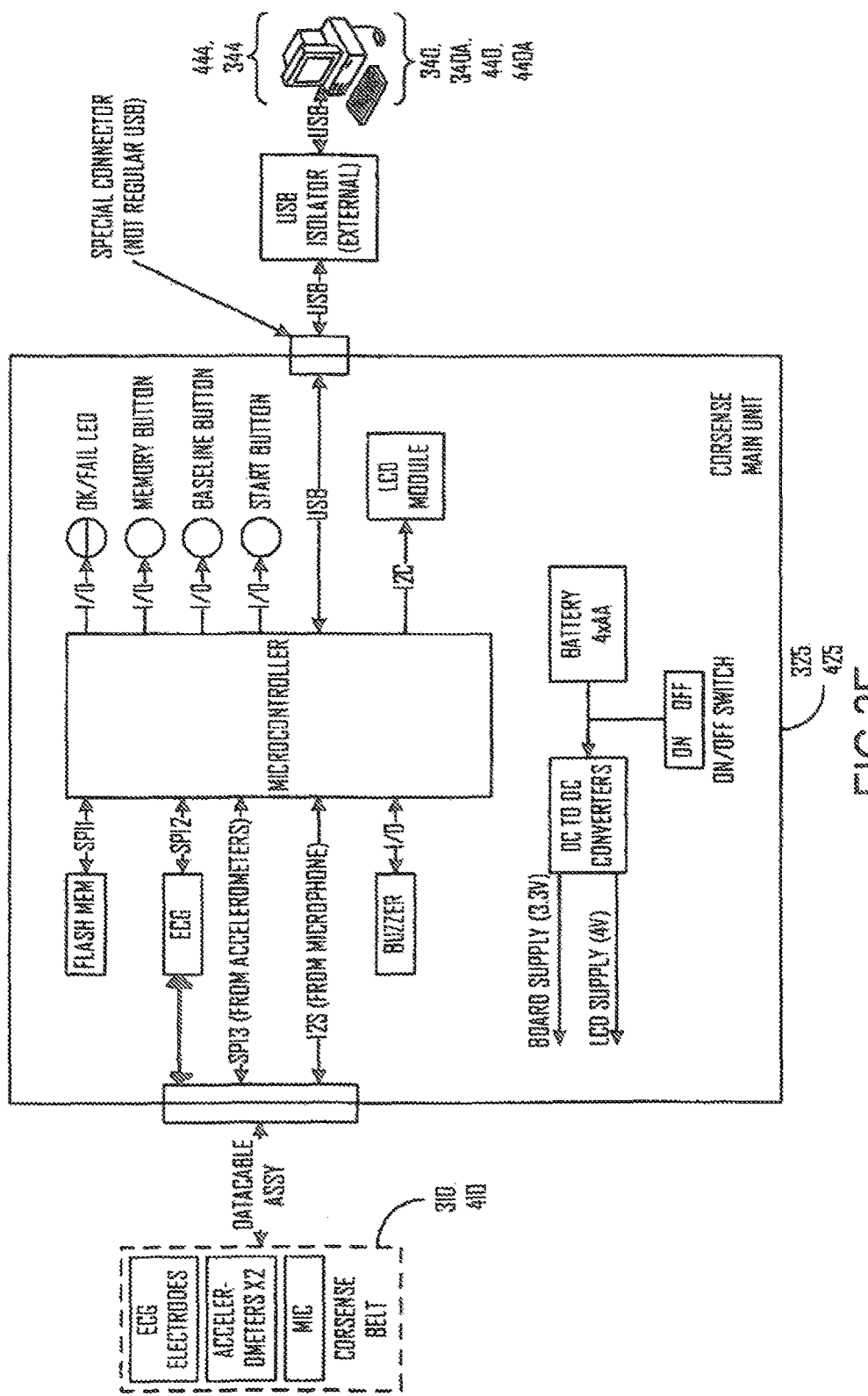
FIG. 3E shows a block diagram of an apparatus, in accordance with one embodiment of the invention.

(D) FIGS. 3C-3D show the main components of apparatus 300, 400 in some embodiments. The operation unit 325, 425 in some embodiments includes hardware 320, 420 and software 330, 430 and in one embodiment is responsible for digitizing the captured data and transmitting the data via a secure USB connection reliably to the application software hosted on a PC. In this embodiment, the operation unit has a Microcontroller (which in this particular embodiment is identified as STM32L151VD Cortex M3) which provides communication of the system with the host PC and the belt. FIG. 3E shows a block diagram of apparatus 300, 400 with three components.

(E) Sensors 311, 411 are attached to the chest in some embodiments and in some embodiments monitor cardiac function by sensing the electrical signal (ECG signals), mechanical vibration correlated signals (contraction) forces and acoustic sound (Microphone) generated by the heart. Apparatus 300, 400 records the movement of the heart during each cardiac cycle (heartbeat) in some embodiments. The heart movement is sensed in certain embodiments by a tri-axial accelerometer (X, Y, Z) aligned to the heart. Electrocardiograph (ECG) signals are sensed and recorded simultaneously with the accelerometers data. The data is analyzed by the dedicated software and displayed on the computer.

(F) Apparatus 300, 400 in one embodiment uses modem digital technology to capture, process, analyze and record the motion of the patient's sternum resulting from the movement of the heart during each cardiac cycle (heart beat). The vibrations, or forces, are detected using high-sensitivity, calibrated, tri-axial accelerometer-based technology. This movement of the heart is sensed by two three-axis accelerometers in this embodiment and is processed digitally and displayed. One accelerometer sensor is located in one embodiment on the sternum and senses all the vibrations ("outside" and heart related). The second accelerometer is isolated from the sternum in this embodiment and senses only the "outside" vibrations. Software 340A, 440A uses an algorithm that in certain embodiments combines and calculates the data from the two accelerometers and provides filtered data of the heart related vibrations. Sensor unit 310, 410 in certain embodiments represents the data of the forces created by the heart and displayed with the acceleration amplitudes as the vertical axis and time as the horizontal axis. The measurements are expressed as milli-gravity over time in milliseconds. Data is displayed on a computer screen of a computer 340, 440 and dedicated software 340A, 440A provides tools for further analysis. The accelerometer data is sensed, recorded and displayed synchronously with the ECG and the Microphone in this embodiment.

(G) Electrocardiograph data is a Trans-Thoracic Echocardiogram (TTE) interpretation of the electrical cavity of the heart over a period of time, as detected by electrodes attached to the surface of the skin and recorded by a device external to the body. An ECG is used to measure the patient heart's electrical conduction system. It picks up electrical impulses generated by the polarization and depolarization of cardiac tissue and translates it into a waveform. Some embodiments of apparatus 300, 400 include an ECG device with an embedded processor containing an ECG data acquisition module, data memory storage, and data processing capabilities. In one embodiment, apparatus 300, 400 reads three leads at a sample rate of 1000 Hz at the following points: LI, LII, LIII, aVL, aVR, aVF and V1-V6. In addition, apparatus 300 in some embodiments automatically filters ECG signal noise sources: filter automatically selected, RFI noise sources, wandering signals, patients' breath artifacts and patient's motion artifacts. The ECG data is sensed, recorded and displayed synchronously with the accelerometer and the Microphone in certain embodiments.

(H) When the myocardium contracts isometrically it generates vibrations which have audible components that are responsible for the first heart sound. The audible spectrum of these vibrations is measured with a microphone in some embodiments. In addition, apparatus 300 in some embodiments is configured to automatically filter Microphone signal noise sources (acoustic sound): filter automatically selected, RFI noise source, wandering signals, patients' breath artifacts and patient's motion artifacts. FIG. 18 shows ECG signals, Accelerometer and Microphone graphs.

(I) Dedicated software 340A, 440A also identifies the time of part of the events in the cardiac cycle in certain embodiments. Cardiac time intervals are regulated by the mechanics and functions of the myocytes; therefore, these intervals are a good measure of the cardiac function. Dedicated software 340A, 440A analyzes the waveforms which are captured from accelerometer and ECG sensors in one embodiment and shows the timing of the following events in the cardiac cycle including: (a) Electromechanical delay (EMD) from R-peak to Mitral valve Closure (MC); (b) Pre-Ejection Time (PET)—from R-peak to aortic valve opening (AO); (c) Isovolumetric Contraction Time (IVCT)—from mitral valve closure to aortic valve opening. The first two points, measured in each cardiac cycle, are used to compute the IsoVolumetric Contraction Time (IVCT=PET−EMD). From the waveforms captured by the accelerometer the PEA is measured and from the PEA and the IVCT, one or more processors execute the dedicated software to compute the MCI. In some embodiments MCI=k·PEA/IVCT, where k is a constant. In one such embodiment, k=1, such that MCI=PEA/IVCT.

(J) Apparatus 300, 400 in some embodiments also displays to a physician the timing of the three following events: Aortic Valve Closed (AVC), Mitral Valve Closed (MVC) and the IsoVolumetric Contraction Time (IVCT). In certain embodiments, apparatus 300, 400 provides accurate timing of part of the event of the cardiac cycle, at least as accurate as an echocardiogram. The vibration peak is known as the Peak Endocardial Acceleration (PEA). PEA is defined as the maximum peak-to-peak amplitude during a window 50 ms before to 200 ms following the peak R wave (ECG). The PEA occurs in the isovolumetric contraction phase.

(K) One particular non-limiting example of the use of the apparatus 300, 400 is as follows. A patient wears the belt 311, 411 of the sensor unit 310, 410 and attaches the sensors 312, 412 of the sensor unit 310, 410 to his or her chest, as described in a user manual. When the patient wears the belt in the correct position, an indication is presented on the LCD screen 325A, 425A of the operation unit 325, 425 and the data capture can begin and the data recording starts. After the patient heart data capture is complete, the operation unit 325, 425 is connected to the PC 340, 440 equipped with the dedicated software, for example via a USB cable. In other embodiments of apparatus 300, 400 some or all data transmission is performed wirelessly. The controlling software application 340A, 440A in some embodiments has the features and functions needed to communicate with and control the sensor unit 310, 410, operation unit 325, 425 and personal computer 340, 440 of apparatus 300, 400. Once communication between the operation unit and the computer, i.e. PC, is established, the software 340A, 440A is configured to stream continuous data from the operation unit 325, 425, record the data streams, and manually analyze the recorded data. In addition, the operation unit's battery status is displayed on the operation unit's LED display. A notification for replacing the battery is presented on the LED display.

The above apparatus 300, 400 is used to implement a wide variety of methods of the invention including any of those described herein. Notwithstanding this, in going from one PEA embodiment to another PEA embodiment, and in going from one MCI embodiment to another MCI embodiment, for example in going from one apparatus or method configured to ascertain a quantitative amount of reperfusion in the myocardium versus another apparatus or method configured to ascertain whether chest pain is or is not cardiac-related, there would be differences in the special purpose software 340A, 440A (and hence there would be differences in what is stored on the memory) and in the step taken by the determination unit or software since the determinations differ. In addition, one would find differences in the output unit 350, 450 and the step of outputting since the outputs and alerts as to what was determined differ.

Figure 6:
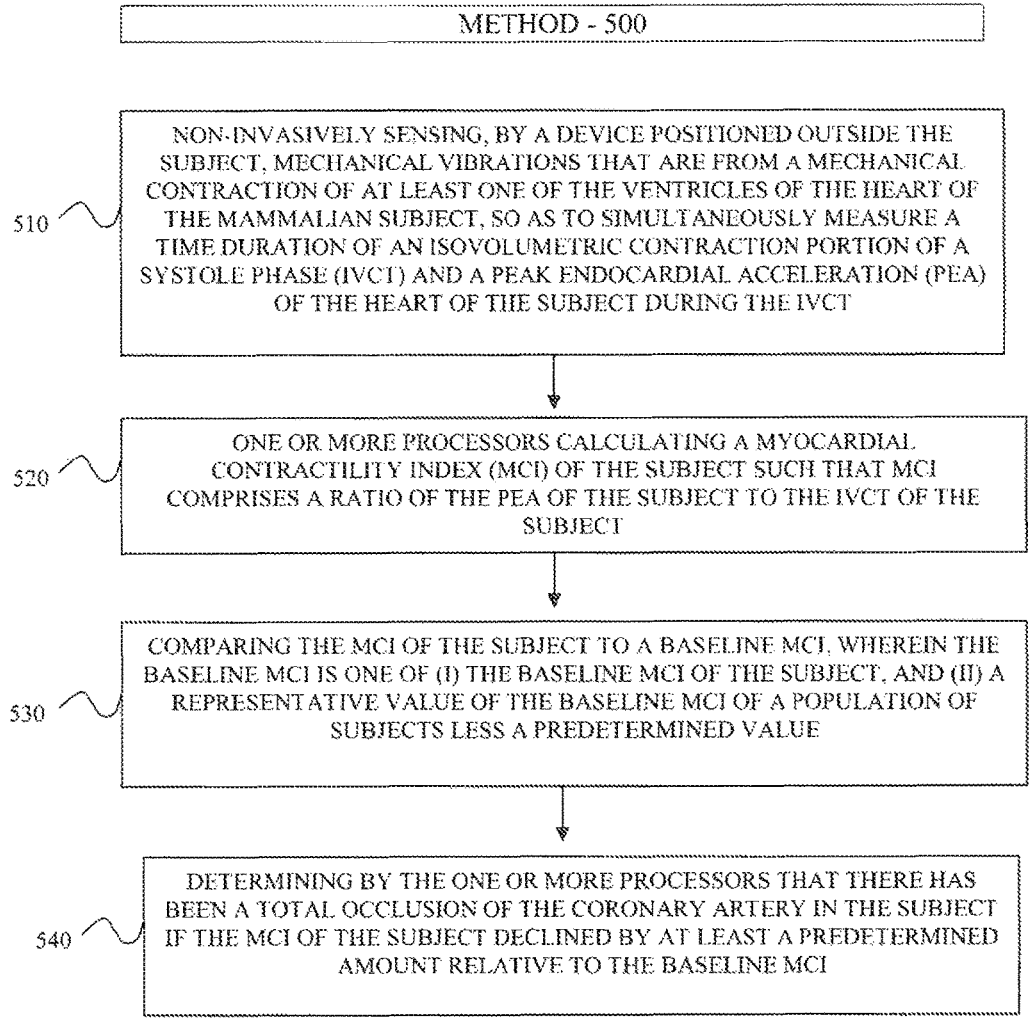
FIG. 6 is a flow chart showing a still further method, in accordance with one embodiment of the invention.

As shown in FIG. 6, the invention, in one embodiment, is a method 500 of detecting a total occlusion of a coronary artery in a mammalian subject that has a heart, the heart including ventricles. Method 500, in one embodiment, comprises a step 510 of, for example by a device positioned outside the subject, non-invasively sensing mechanical vibrations that are from a mechanical contraction of at least one of the ventricles of the heart of the mammalian subject, so as to simultaneously in some embodiments measure (a) IVCT, wherein in some embodiments IVCT is a time duration of an isovolumetric contraction portion of a systole phase of a cardiac cycle of the subject; and (b) a peak endocardial acceleration (PEA) of the heart of the subject for example during the IVCT.

Method 500 also includes a step 520 in some embodiments of calculating, for example dynamically, a myocardial contractility index (MCI) of the subject such that the MCI comprises a ratio of the PEA of the subject to the IVCT of the subject. The MCI is calculated in some embodiments by one or more processors directly or indirectly from signals corresponding to the sensed mechanical vibrations. In some embodiments, MCI=k·PEA/IVCT, where k is a constant. In certain embodiments, k=1, such that MCI=PEA/IVCT. The step of calculating MCI in some embodiments is done dynamically such that as the PEA is being measured, the one or more processors is/are dynamically calculating the MCI. In other embodiments, the MCI is calculated only at select junctures of method 500.

Method 500 in some embodiments has a step 530 of comparing the MCI of the subject during the sensing period to a baseline MCI, wherein the baseline MCI is one of (i) the baseline MCI of the subject, and (ii) a representative value of the baseline MCI of a population of subjects less a predetermined value. The predetermined value is for example a number of standard deviations, for example two, from the representative value (the representative value being for example a mean, median, average or other representative value), which in some cases is a "mean normal value" of the baseline MCI of a population of subjects, as that term has been previously explained.

Method 500 in some embodiments has a step 540 of determining that there has been a total occlusion of the coronary artery in the subject if the MCI of the subject declined during the sensing period by at least a predetermined amount relative to the baseline MCI. In some case, method 500 has a step of determining that there has been a total occlusion of the coronary artery in the subject if the MCI of the subject declined during the sensing period by at least one-fifth relative to the baseline MCI. Instead of one-fifth in some embodiments the predetermined amount relative to the baseline MCI is a certain fraction of the baseline MCI of between one-tenth and three-tenths or 16% or 19% or 24% or 28% or 33% or 40% or 50% or 60% any number in between. These numbers are only non-limiting examples of predetermined amounts.

Figure 7:
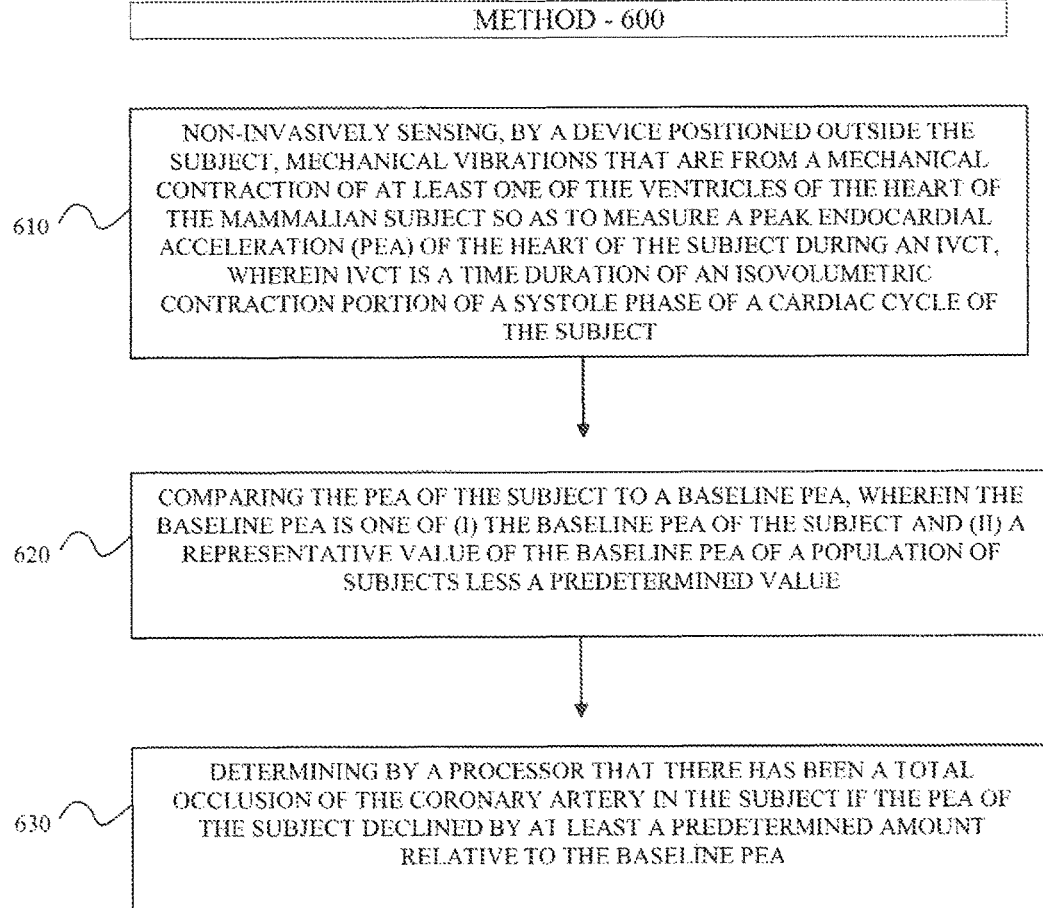
FIG. 7 is a flow chart showing a yet still further method, in accordance with one embodiment of the invention.

As shown in FIG. 7, in a further embodiment, the invention is a method 600 of detecting a total occlusion of a coronary artery in a mammalian subject that has a heart, the heart including ventricles. Method 600 includes a step 610 in some embodiments of non-invasively sensing mechanical vibrations that are from a mechanical contraction of at least one of the ventricles of the heart of the mammalian subject so as to measure a peak endocardial acceleration (PEA) of the heart of the subject for example during an IVCT, wherein IVCT is a time duration of an isovolumetric contraction portion of a systole phase of a cardiac cycle of the subject. Method 600 has a further step 620 in some embodiments of comparing the PEA of the subject during the sensing period to a baseline PEA, wherein the baseline PEA is (i) the baseline PEA of the subject or (ii) a representative value of the baseline PEA of a population of subjects less a predetermined value. The predetermined value is for example a predetermined number of standard deviations, for example two standard deviations, from the representative value (the representative value being for example a mean, median, average or other representative value), which in some cases is a mean normal value, of the baseline PEA of a population of subjects. The population of subjects is for example a population of subjects other than the subject being diagnosed.

Method 600 also has in some embodiments a further step 630 of determining that there has been a total occlusion of the coronary artery in the subject if the PEA of the subject declined during the sensing period by at least a predetermined amount relative to the baseline PEA. For example, method 600 has a step in some embodiments of determining that there has been a total occlusion of the coronary artery in the subject if the PEA of the subject declined during the sensing period by at least one-tenth relative to the baseline PEA, or by a certain fraction of the baseline PEA between one twentieth and one fifth or 9% or 11% or 12% or 13% or 14% or 15% or 16% or 17% or 18% or another percent (since these numbers are only non-limiting examples of predetermined amounts relative to the baseline PEA).

An extension of methods 500 and 600 is an embodiment of the invention in which beyond determining total occlusion, one also determines an acute myocardial infarction. For example, if the determination being made is not just total occlusion but also that the total occlusion persisted for a predetermined amount of time, for example at least 30 minutes, or at least 40 minutes or at least 50 minutes or at least 60 minutes (or another amount of time between 25 and 65 minutes) then it is determined that the patient suffered an acute myocardial infarction caused by the total occlusion. For example, method 500 and method 600 each have, in certain embodiments, a further step of repeating, or dynamically repeating, the sensing, calculating, comparing, determining of MCI or the sensing, comparing, determining of the PEA, so as to determine acute myocardial infarction from a determination that the decline in MCI or PEA sufficient to trigger the determination of total occlusion persisted for at least the predetermined amount of time, such as 30 minutes or some other specified amount of time falling between a range of 30 to 60 minutes. This further step, in some embodiments comprises repeating the sensing, calculating, comparing and determining steps (i.e. steps 510, 520, 530 and 540) for method 500 or repeating the sensing, comparing and determining steps (i.e. steps 610, 620 and 630) for method 600, for example 25 or 30 minutes later or 40 minutes later or 50 minutes later or 60 or 65 minutes later (or another amount of time later between 25 and 65 minutes later) so as to determine that at least a predetermined amount of time has passed since the total occlusion (i.e. the total occlusion has persisted for at least that predetermined amount of time) and that therefore an acute myocardial infarction has occurred, wherein the predetermined amount of time falls within 25 to 65 minutes (for example at least 30 minutes or at least 60 minutes).

Figure 8:
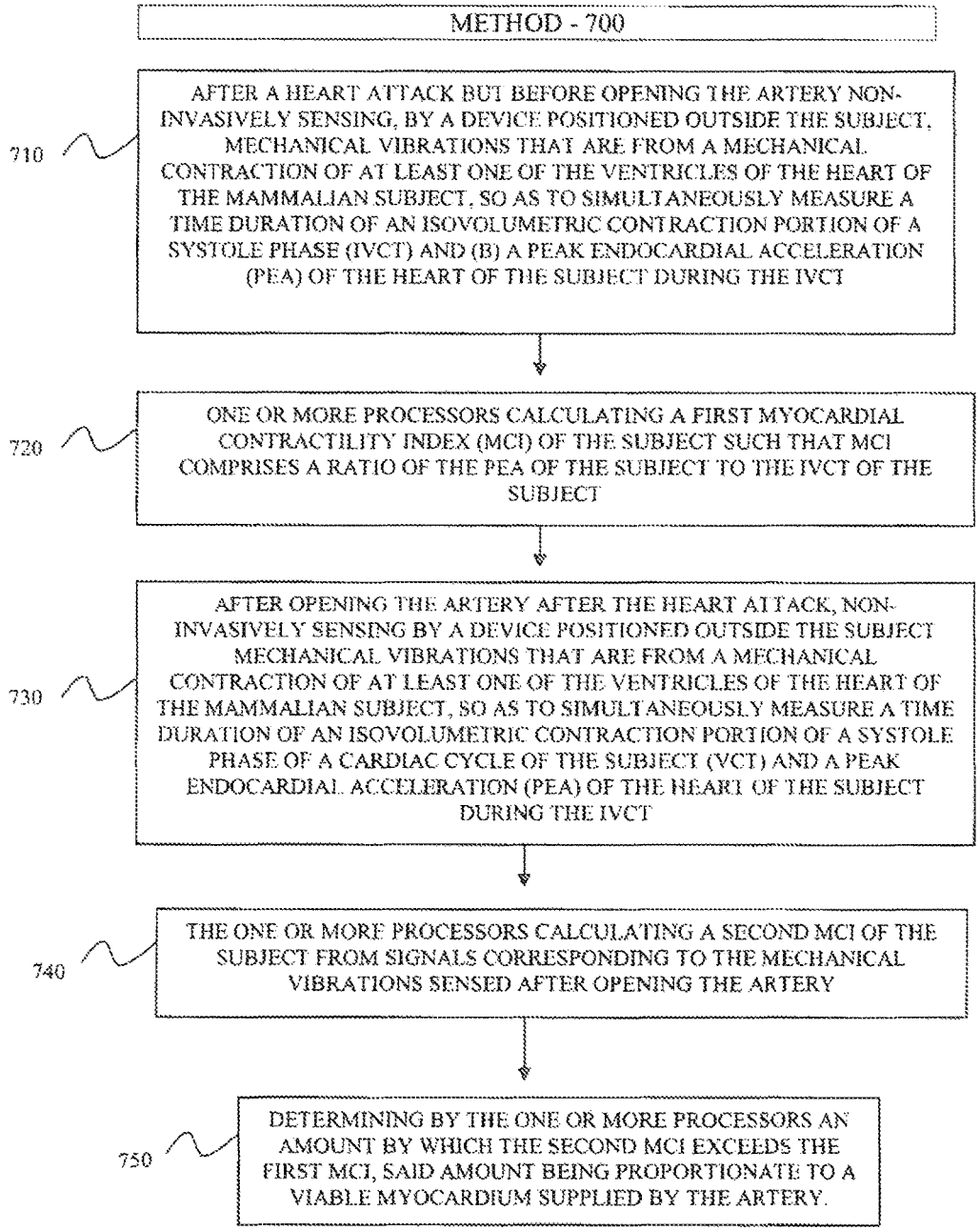
FIG. 8 is a flow chart showing a still further method, in accordance with one embodiment of the invention.

A still further embodiment of the invention shown in FIG. 8 is a method 700 of determining an amount of viable (or salvageable) myocardium supplied by an artery of a mammalian subject after a heart attack of the mammalian subject. Method 700 comprises a step 710 in some embodiments of during a first sensing period after a heart attack but before opening the artery, i.e. angioplasty, non-invasively sensing, for example by a device positioned outside the subject, mechanical vibrations that are from a mechanical contraction of at least one of the ventricles of the heart of the mammalian subject, so as to simultaneously measure (a) IVCT, wherein IVCT is for example a time duration of an isovolumetric contraction portion of a systole phase of a cardiac cycle of the subject; and (b) a peak endocardial acceleration (PEA) of the heart of the subject during the IVCT.

Method 700 has in some embodiments a step 720 of calculating a first myocardial contractility index (MCI) of the subject such that MCI comprises a ratio of the PEA of the subject to the IVCT of the subject. In some embodiments this ratio is MCI=k·PEA/IVCT, where k is a constant. In one such embodiment, k=1 such that the ratio is MCI=PEA/IVCT.

The step of calculating the MCI in some embodiments is done dynamically such that as the PEA is being measured one or more processors are dynamically calculating the MCI. In other embodiments, the MCI is calculated only at select junctures of method 500. The step of calculating is done from digital signals derived from analog signals that correspond to the sensed mechanical vibrations.

Method 700 has in some embodiments a step 730 of, during a second sensing period, after a heart attack but before opening the artery non-invasively sensing, for example by a device positioned outside the subject, mechanical vibrations that are from a mechanical contraction of at least one of the ventricles of the heart of the mammalian subject, so as to simultaneously measure (a) IVCT, wherein IVCT is a time duration of an isovolumetric contraction portion of a systole phase of a cardiac cycle of the subject; and (b) a peak endocardial acceleration (PEA) of the heart of the subject during the IVCT.

Method 700 has in some embodiments a step 740 of calculating a second MCI of the subject, for example directly or indirectly from signals corresponding to the mechanical vibrations sensed during the second period.

Method 700 in some embodiments has a step 750 of determining, for example by a processor, an amount by which the second MCI exceeds the first MCI, said amount being proportionate to a viable myocardium supplied by the artery.

A further embodiment of the invention is a non-invasive apparatus 400 configured to non-invasively determine an amount of reperfusion of blood to a myocardium supplied by an artery of a mammalian subject after a heart attack of the mammalian subject. The apparatus 400 may comprise a sensor unit 410 configured to non-invasively sense from outside the subject mechanical vibrations that are from a mechanical contraction of at least one of the ventricles of the heart of the mammalian subject so as to simultaneously measure (a) IVCT, wherein IVCT is a time duration of an isovolumetric contraction portion of a systole phase of a cardiac cycle of the subject; and (b) a peak endocardial acceleration (PEA) of the heart of the subject during the IVCT. The apparatus 400 may also include a determination unit 444 comprising one or more processors 440 programmed by software stored on a memory. The determination unit 444 may be configured to receive digital signals corresponding to the sensed mechanical vibrations, and to determine the PEA during the IVCT. The determination unit 444 may include a perfusion module for determining, by one or more processors 440, that execute program code 440A (for example software 440A) stored on memory 440B, an amount of reperfusion in the myocardium. The perfusion module in one embodiment is part of the program code 440A executed by the one or more processors 440 of the determination unit 444. The determination unit 444 may accomplish this by the one or more processors 440 comparing a first PEA of the subject sensed by the sensor unit 410 after a heart attack but before opening the artery to a second PEA of the subject sensed by the sensor unit 410 at a subsequent time after opening the artery. The amount of reperfusion is expected to be proportionate to how much viable myocardium (supplied by the artery) remains in the subject. The determination unit 444 may be configured to determine a degree of restoration of function of the subject's heart derived from the opening of the artery.

For example, one typically would not have a baseline reference for PEA (or a baseline MCI, which is calculated from PEA) for a patient who has suffered a heart attack. Accordingly, in one embodiment, the effective baseline that is used is the PEA level of the subject taken after the heart attack but before the opening of the artery (for example using angioplasty) which is referred to herein as "first PEA". In one non-limiting example, the first PEA taken is equal to 6,000 in units of acceleration units (for example dP/dtmax or an equivalent number in units of G or milig) for a particular subject. The second PEA taken later after the artery has been opened, for example using angioplasty, is equal to 7,200 in the same units of acceleration. According to this, in this case one concludes that there has been 20% reperfusion. In some embodiments, one assumes that the population of subjects that this subject fits into would normally have a PEA equal to 20,000 in the same units of acceleration. Under this assumption, reperfusion has been only partial. But the determination of the amount of reperfusion in the myocardium of the subject is very useful information for a number of reasons. It helps determine the severity of the heart attack (for example, mild, moderate, severe). It helps determine the degree (especially a quantitative degree) of restoration of function of the subject's heart derived from the procedure, i.e. angioplasty. It also may yield a measure, i.e. a quantitative measure, of contractile reserve in the patient, which has great importance regarding the future of the patient.

Since the pre-myocardial infarction PEA is typically unknown, one always assumes a partial restoration of function since one never knows the exact pre-MI PEA. However, if the second PEA is close enough to the normal values based on the population of subjects that the subject fits into, one assumes that it is a complete or near complete reperfusion and a near or complete restoration of function. In contrast, if the second PEA stayed well below normal values (as defined by the population of subjects that the subject fits into) one concludes that the reperfusion was a partial reperfusion and the restoration of function was a partial restoration of function.

The output unit 450, in one embodiment, may output a percentage or other quantitative measure of reperfusion, or in other embodiments a range or a category (by way of non-limiting example, "partial", "moderate", "near complete", "complete") of reperfusion in the myocardium. In another embodiment, output unit 450 outputs raw data of the first PEA and second PEA. In still another embodiment, output unit 450 outputs a quantitative amount, a range a degree or a category (i.e. partial, moderate, near complete, complete) of restoration of function. In another embodiment, the output unit 450 outputs an amount, a percentage, or other quantitative measure, or a range or a category, of viable myocardium. For example, output unit 450, in one embodiment, outputs at least 20% increase of the second PEA over the first PEA or at least 20% reperfusion, or at least another percentage used as a metric of reperfusion. It is apparent that medical practitioners will use output unit 450 to output different useful outputs as needed and that such outputs could for example include ratios of the second PEA to the first PEA or other mathematical functions describing a relationship between the second PEA to the first PEA or vice versa.

The following applies to all embodiments based on reperfusion. Since there is no real baseline for the subject after a heart attack and the first PEA or the first MCI is used as the effective baseline for measuring the amount of reperfusion, then in some embodiments there is a predefined mathematical relationship between the second PEA and the first PEA (or between the second MCI and the first MCI) that provides a metric for assessing that reperfusion has occurred to a defined extent or to a satisfactory extent or that provides a metric for assessing that thrombolysis has been effective.

As shown in Tables 1-10 and FIG. 14, the trial that Applicant conducted on 27 subjects mimicked reperfusion. Applicant measured the PEA at the beginning after 25 seconds of occlusion with a balloon and saw a decrease in PEA compared to a baseline, which means ischemia. Then Applicant opened the balloon creating reperfusion. Applicant saw that PEA returned immediately to baseline values. So one can use differentials in PEA to detect the amount of the return of blood to the myocardium (reperfusion) and the return of function, even though the situation of a heart attack is somewhat different, since the principle is the same.

Figure 9:
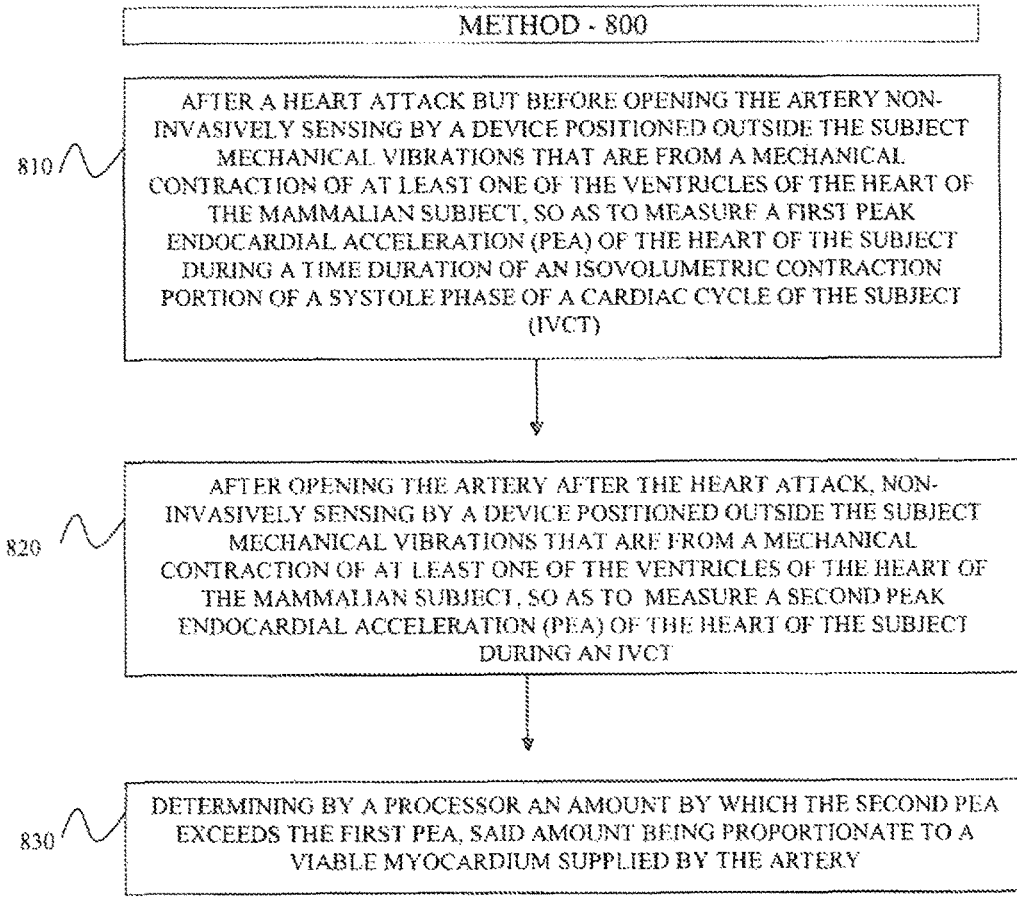
FIG. 9 is a flow chart showing a yet still further method, in accordance with one embodiment of the invention.
Figure 9A:
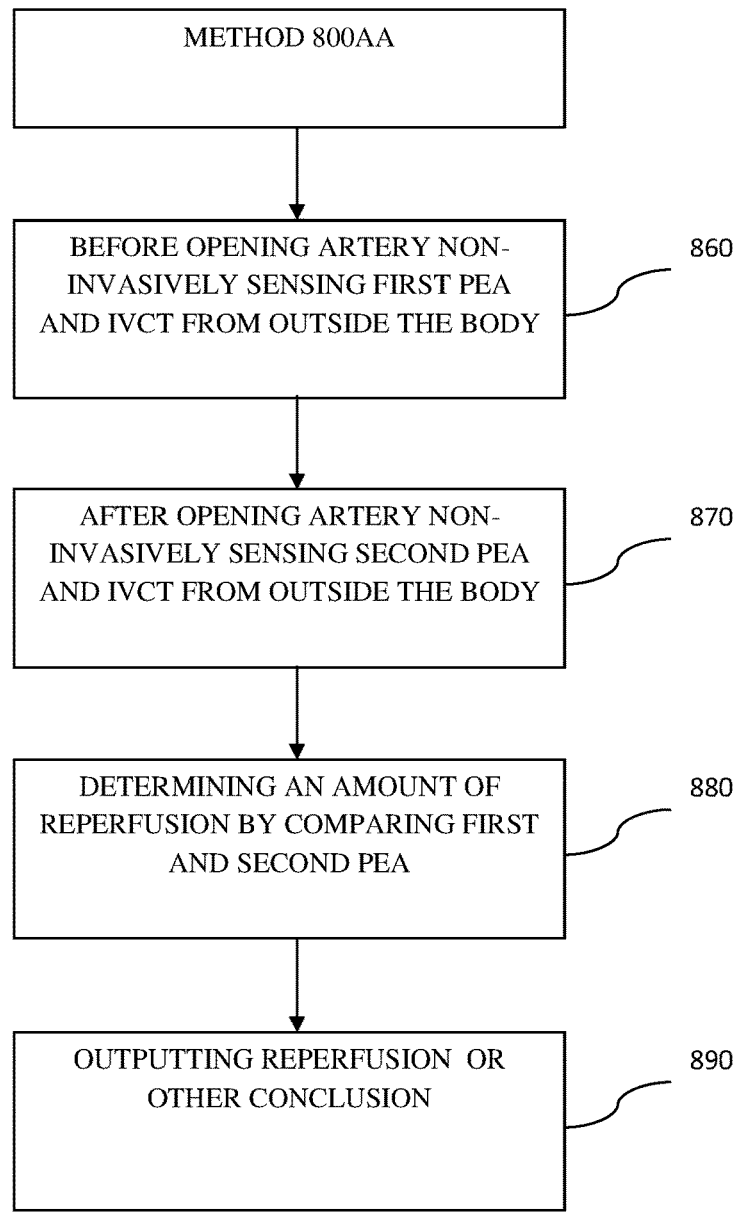
FIG. 9AA is a flow chart showing a yet still further method, in accordance with one embodiment of the invention.

A further embodiment shown in FIG. 9AA is a method that parallels the apparatus 400 just described in regard to determining an amount of re-perfusion. This embodiment is a method 800AA of non-invasively determining an amount of reperfusion in a myocardium supplied by an artery of a mammalian subject after a heart attack of the mammalian subject. Method 800AA may comprise a step 860 of, after a heart attack but before opening the artery non-invasively sensing by a device positioned outside the subject mechanical vibrations that are from a mechanical contraction of at least one of the ventricles of the heart of the mammalian subject, so as to measure a first peak endocardial acceleration (PEA) of the heart of the subject during an IVCT wherein IVCT is a time duration of an isovolumetric contraction portion of a systole phase of a cardiac cycle of the subject.

Method 800AA may also comprise as a step 870 of, after opening the artery after the heart attack, non-invasively sensing by a device positioned outside the subject mechanical vibrations that are from a mechanical contraction of at least one of the ventricles of the heart of the mammalian subject, so as to measure a second peak endocardial acceleration (PEA) of the heart of the subject during an IVCT.

A further step 880 of method 800AA may be determining, by one or more processors, an amount of reperfusion in the myocardium by comparing an amount by which the second PEA exceeds the first PEA. The determining may also include applying a mathematical function such as a percentage or a ratio or applying a range or a category to describe the amount of reperfusion. The method 800AA may also include a step 890 of outputting an alert or an output or conclusion of how much reperfusion occurred, how much restoration of function occurred derived from the opening of the artery, how much viable myocardium remains or any combination thereof. Generally, the amount of reperfusion is proportionate to the amount of viable myocardium that exists in the subject.

The invention also includes embodiments that parallel the apparatus 400 configured for determining an amount of reperfusion and method 800AA in which MCI is calculated from the PEA. For example, one embodiment of the invention is a non-invasive apparatus 300 configured to non-invasively determine an amount of reperfusion of blood to a myocardium supplied by an artery of a mammalian subject after a heart attack of the mammalian subject, the apparatus 300 comprising: a sensor unit 310 configured to non-invasively sense from outside the subject mechanical vibrations that are from a mechanical contraction of at least one of the ventricles of the heart of the mammalian subject so as to simultaneously measure (a) IVCT, wherein IVCT is a time duration of an isovolumetric contraction portion of a systole phase of a cardiac cycle of the subject; and (b) a peak endocardial acceleration (PEA) of the heart of the subject during the IVCT. Apparatus 300 may also include a determination unit 344 comprising one or more processors 340 programmed by software 340A stored on a memory 340B.

The determination unit 344 may be configured to receive digital signals corresponding to the sensed mechanical vibrations, and to determine the PEA during the IVCT, the one or more processors configured to also calculate a first myocardial contractility index (MCI) of the subject such that MCI comprises a ratio of the PEA of the subject to the IVCT of the subject, the determination unit 344 may include a perfusion module for determining, by the one or more processors 340 programmed by program code 440A (for example software 440A), an amount of reperfusion in the myocardium by comparing a first MCI of the subject sensed by the sensor unit after a heart attack but before opening the artery to a second MCI of the subject sensed by the sensor unit at a subsequent time after opening the artery. The perfusion module in one embodiment is part of the program code 340A executed by the one or more processors 340 of the determination unit 344.

The various types of outputs produced by an output unit 350 that may be included in apparatus 300 (for providing outputs relating to the amount of reperfusion), have already been described in connection with the output unit 450 of apparatus 400 (for providing outputs relating to the amount of reperfusion). The amount of reperfusion is in one embodiment considered proportionate to the amount of viable myocardium supplied by the artery. Determination unit 344 may be configured to determine a degree of restoration of function of the subject's heart derived from the opening of the artery.

Figure 8A:
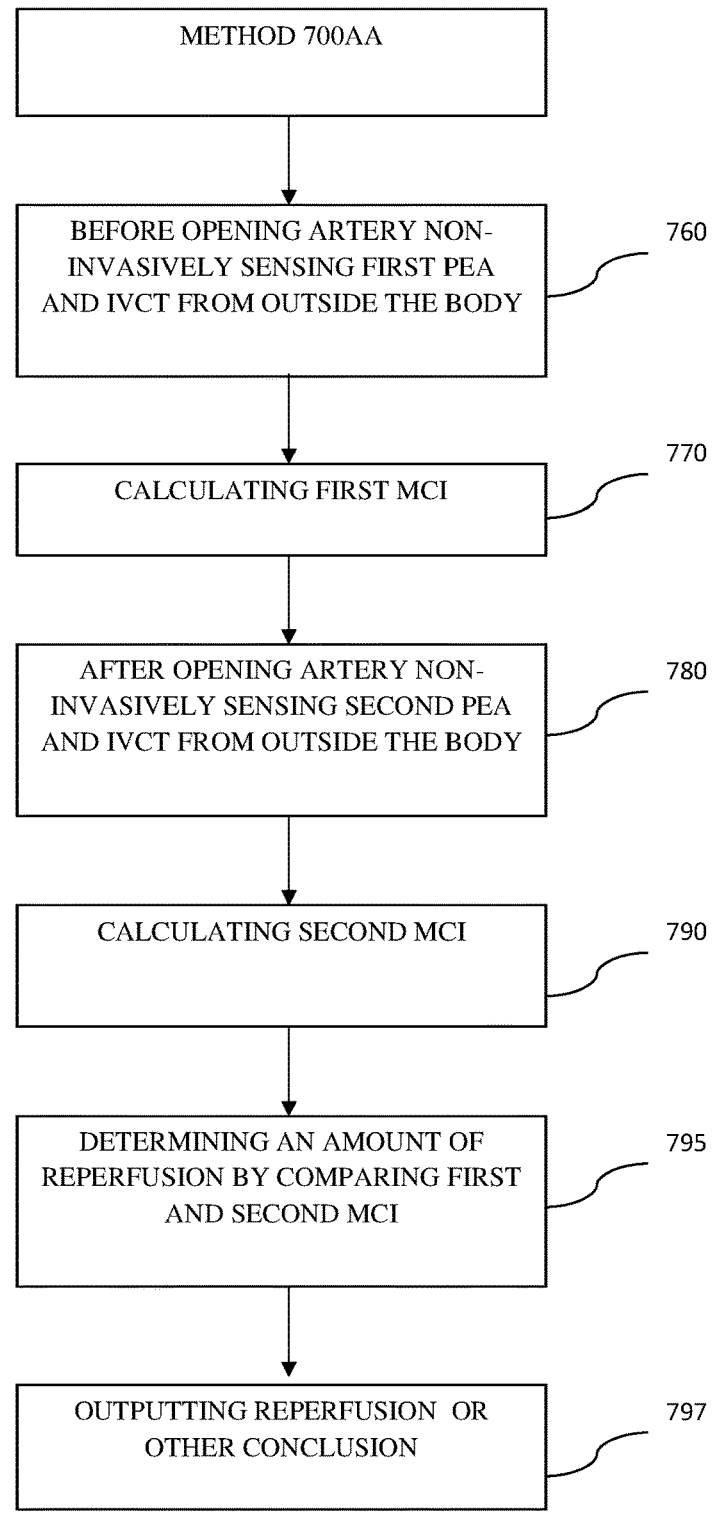
FIG. 8AA is a flow chart showing a still further method, in accordance with one embodiment of the invention.

One embodiment of the invention is a method 700AA (as shown in FIG. 8AA) of non-invasively determining an amount of reperfusion in a myocardium supplied by an artery of a mammalian subject after a heart attack of the mammalian subject. This method 700AA tracks method 800AA except that MCI is calculated from PEA. For example, method 700AA has a step 760 of, after a heart attack but before opening the artery non-invasively sensing by a device positioned outside the subject mechanical vibrations that are from a mechanical contraction of at least one of the ventricles of the heart of the mammalian subject, so as to simultaneously measure a first IVCT, wherein IVCT is a time duration of an isovolumetric contraction portion of a systole phase of a cardiac cycle of the subject, and a first peak endocardial acceleration (PEA) of the heart of the subject during the first IVCT. A further step 770 of method 700AA is calculating, by one or more processors, a first myocardial contractility index (MCI) of the subject, wherein the first MCI comprises a ratio of the first PEA of the subject to the first IVCT of the subject.

Method 700AA has another step 780 of, after opening the artery after the heart attack, non-invasively sensing by a device positioned outside the subject mechanical vibrations that are from a mechanical contraction of at least one of the ventricles of the heart of the mammalian subject, so as to simultaneously measure a second IVCT and a second peak endocardial acceleration (PEA) of the heart of the subject during the second IVCT.

A further step 790 of method 700AA is calculating, by one or more processors, a second myocardial contractility index (MCI) of the subject wherein the second MCI comprises a ratio of the second PEA of the subject to the second IVCT of the subject; and determining, by one or more processors, an amount of reperfusion in the myocardium, by comparing an amount by which the second MCI exceeds the first MCI. It is understood that the amount of reperfusion is proportionate to a viable myocardium supplied by the artery. Method 700AA may include a step 795 of determining, by the one or more processors, a degree of restoration of function of the subject's heart derived from the opening of the artery. Optionally, there is a step 797 of outputting In a further embodiment shown in FIG. 9, the invention is a method 800 of determining an amount of viable or salvageable myocardium supplied by an artery of a mammalian subject after a heart attack of the mammalian subject. Method 800 comprises in some embodiments a step 810 of during a first sensing period after a heart attack but before opening the artery non-invasively sensing, for example by a device positioned outside the subject, mechanical vibrations that are from a mechanical contraction of at least one of the ventricles of the heart of the mammalian subject, so as to measure a first peak endocardial acceleration (PEA) of the heart of the subject during an IVCT wherein IVCT is a time duration of an isovolumetric contraction portion of a systole phase of a cardiac cycle of the subject.

Method 800 in some embodiments has a further step 820 of, during a second sensing period after opening the artery after the heart attack, non-invasively sensing, for example by a device positioned outside the subject, mechanical vibrations that are from a mechanical contraction of at least one of the ventricles of the heart of the mammalian subject, so as to measure a second peak endocardial acceleration (PEA) of the heart of the subject during an IVCT. Method 800 has a step 830 in some embodiments of determining, by a processor, an amount by which the second PEA exceeds the first PEA, said amount being proportionate to a viable myocardium supplied by the artery.

Apparatus 400, in a further embodiment, is configured to assess an effectiveness of thrombolysis from an amount of reperfusion of blood. In this embodiment, a non-invasive apparatus 400 configured to non-invasively assess an effectiveness of thrombolysis on a clot in an artery of a mammalian subject after a heart attack of the mammalian subject by determining an amount of reperfusion in the artery, comprises a sensor unit 410 configured to non-invasively sense from outside the subject mechanical vibrations that are from a mechanical contraction of at least one of the ventricles of the heart of the mammalian subject so as to simultaneously measure (a) IVCT, wherein IVCT is a time duration of an isovolumetric contraction portion of a systole phase of a cardiac cycle of the subject; and (b) a peak endocardial acceleration (PEA) of the heart of the subject during the IVCT. Apparatus 400 also comprises a determination unit 444 comprising one or more processors 440 programmed by software 440A stored on a memory 440B. Determination unit 444 may be configured to receive digital signals corresponding to the sensed mechanical vibrations, and to determine the PEA during the IVCT. Determination unit 444 may include a perfusion module, which may be part of program code 440A, for determining, by one or more processors, an amount of reperfusion in the artery by comparing a first PEA of the subject sensed by the sensor unit after a heart attack but before the thrombolysis to a second PEA of the subject sensed by the sensor unit after the thrombolysis. Apparatus 400 may include an output unit 450 that outputs an alert or a quantitative (or other) assessment of the effectiveness of the thrombolysis in any form, including a difference between the first PEA and the second PEA in absolute amount or percentage or a ratio or other function, as well as any category or range describing the effectiveness (mildly effective moderately effective, very effectiveness, almost completely effective, completely effective, effective to the following numerical amount etc.). The output may include for example that the PEA has increased by at least 20% or by at least some other pre-determined metric of effectiveness, or metric or a degree of effectiveness. Since the effectiveness of the thrombolysis is based on or proportionate to the amount of reperfusion in the artery after the thrombolysis as compared to before the thrombolysis, the output may also be in the form of an amount or percentage or other ratio of description of the reperfusion as described above in regard to other reperfusion embodiments. The amount of reperfusion determines the assessment of the effectiveness of the thrombolysis. The determination unit 444 may be configured to determine a degree of restoration of function of the subject's heart derived from the thrombolysis in any of the above forms (an absolute amount, a percentage at least such and such percentage, at least 20%, or a grade or range or a category of effectiveness (moderately, partially, almost completely, completely effective, etc.).

Figure 10:
FIG. 10 is a flow chart showing a further method, in accordance with one embodiment of the invention.
Figure 10:
Figure 10:
Figure 10:
Figure 10:
Figure 10A:
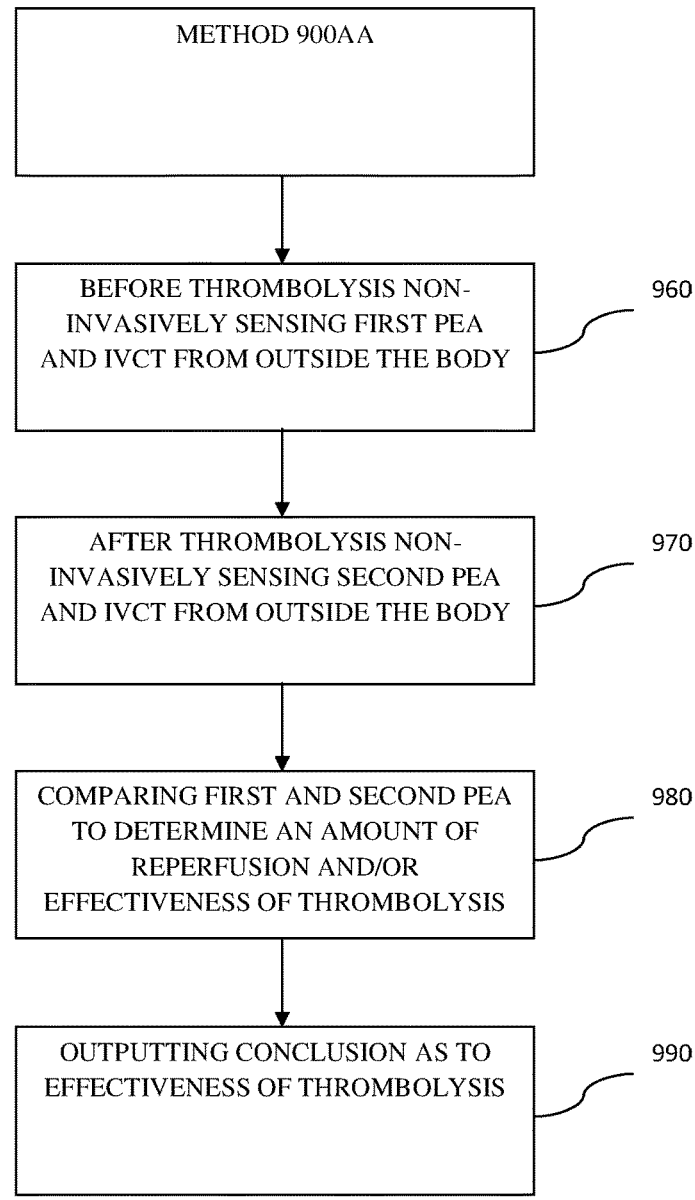
FIG. 10AA is a flow chart showing a further method, in accordance with one embodiment of the invention.

As shown in FIG. 10AA, there is a method 900AA that parallels the just described apparatus 400. Method 900AA is a method of non-invasively assessing an effectiveness of thrombolysis on a clot in an artery of a mammalian subject after a heart attack of the mammalian subject by determining an amount of reperfusion in the artery. Method may comprise a step 960 of, after a heart attack but before thrombolysis, non-invasively sensing by a device positioned outside the subject mechanical vibrations that are from a mechanical contraction of at least one of the ventricles of the heart of the mammalian subject, so as to measure a first peak endocardial acceleration (PEA) of the heart of the subject during an IVCT wherein IVCT is a time duration of an isovolumetric contraction portion of a systole phase of a cardiac cycle of the subject.

A further step 970 of method 900AA is, after the thrombolysis to dissolve the clot, non-invasively sensing by a device positioned outside the subject mechanical vibrations that are from a mechanical contraction of at least one of the ventricles of the heart of the mammalian subject, so as to measure a second peak endocardial acceleration (PEA) of the heart of the subject during an IVCT.

Method 900AA may also comprise a step 980 of determining, by one or more processors, an amount of reperfusion in the artery by comparing an amount by which the second PEA exceeds the first PEA. Method 900AA may also have a step 990 of outputting, using an output unit 350, an alert or a quantitative (or other) assessment of the effectiveness of the thrombolysis in any form, including a difference between the first PEA and the second PEA in absolute amount or percentage or a ratio or other function, as well as any category or range describing the effectiveness (mildly effective moderately effective, very effectiveness, almost completely effective, completely effective, effective to the following numerical amount etc.). Since the effectiveness of the thrombolysis is based on or proportionate to the amount of reperfusion in the artery after the thrombolysis as compared to before the thrombolysis, the output may be in the form of an amount or percentage or other ratio of description of the reperfusion as described above in regard to other reperfusion embodiments. Method 900AA may also include a step of determining, by the one or more processors, a degree of restoration function of the subject's heart derived from the thrombolysis.

The following embodiment is of the apparatus 300 used for assessing the effectiveness of thrombolysis based on the amount of reperfusion but with the calculation of MCI. This tracks the description and details of the embodiment of apparatus 400 used for assessing the effectiveness of thrombolysis based on the amount of reperfusion as described above based on PEA (without MCI). To summarize, the embodiment is a non-invasive apparatus 300 configured to non-invasively assess an effectiveness of thrombolysis on a clot in an artery of a mammalian subject after a heart attack of the mammalian subject by determining an amount of reperfusion in the artery. The apparatus 300 may comprise a sensor unit 310 configured to non-invasively sense from outside the subject mechanical vibrations that are from a mechanical contraction of at least one of the ventricles of the heart of the mammalian subject so as to simultaneously measure (a) IVCT, wherein IVCT is a time duration of an isovolumetric contraction portion of a systole phase of a cardiac cycle of the subject; and (b) a peak endocardial acceleration (PEA) of the heart of the subject during the IVCT.

Apparatus 300 may comprise a determination unit 344 comprising one or more processors 340 programmed by software 340A stored on a memory 340B, the determination unit 344 configured to receive digital signals corresponding to the sensed mechanical vibrations, and to determine the PEA during the IVCT, the one or more processors 340 configured to also calculate a first myocardial contractility index (MCI) of the subject such that MCI comprises a ratio of the PEA of the subject to the IVCT of the subject.

Determination unit 344 may include a perfusion module (which may be part of the software or program code 340A) for determining, by the one or more processors 340, an amount of reperfusion in the artery by comparing a first MCI of the subject sensed by the sensor unit after a heart attack but before the thrombolysis to a second MCI of the subject sensed by the sensor unit after the thrombolysis. The output unit 350 outputs, an alert or a quantitative (or other) assessment of the effectiveness of the thrombolysis in any form, including a difference between the first PEA and the second PEA in absolute amount or percentage or a ratio or other function, as well as any category or range describing the effectiveness (mildly effective moderately effective, very effectiveness, almost completely effective, completely effective, effective to the following numerical amount etc.). Since the effectiveness of the thrombolysis is based on or proportionate to the amount of reperfusion in the artery after the thrombolysis as compared to before the thrombolysis, the output may be in the form of an amount or percentage or other ratio of description of the reperfusion as described above in regard to other reperfusion embodiments. The output may also include a degree of restoration function of the subject's heart derived from the thrombolysis since the assessment of the effectiveness of the thrombolysis may be based on the amount of reperfusion.

Figure 11:
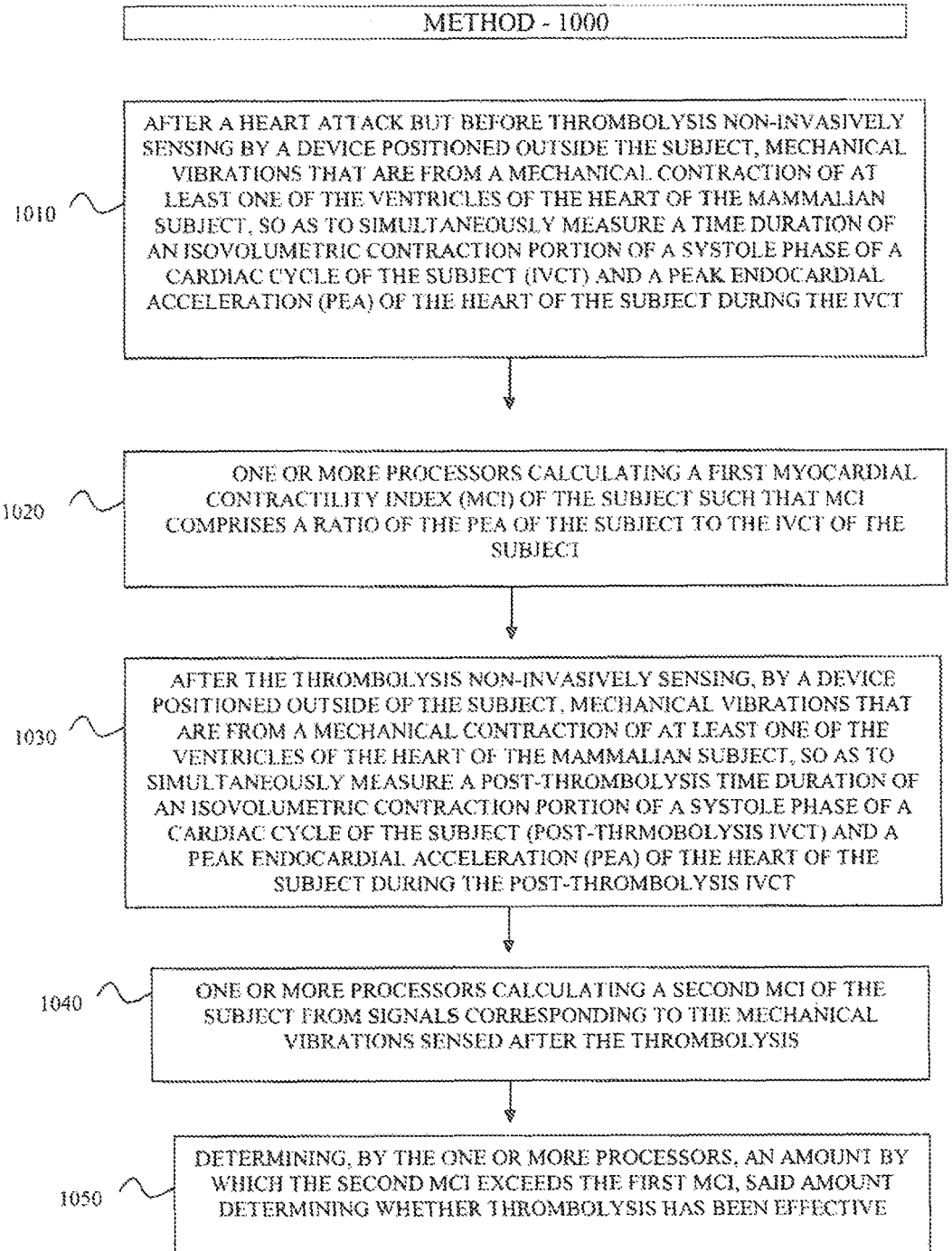
FIG. 11 is a flow chart showing a yet still further method, in accordance with one embodiment of the invention.
Figure 11A:
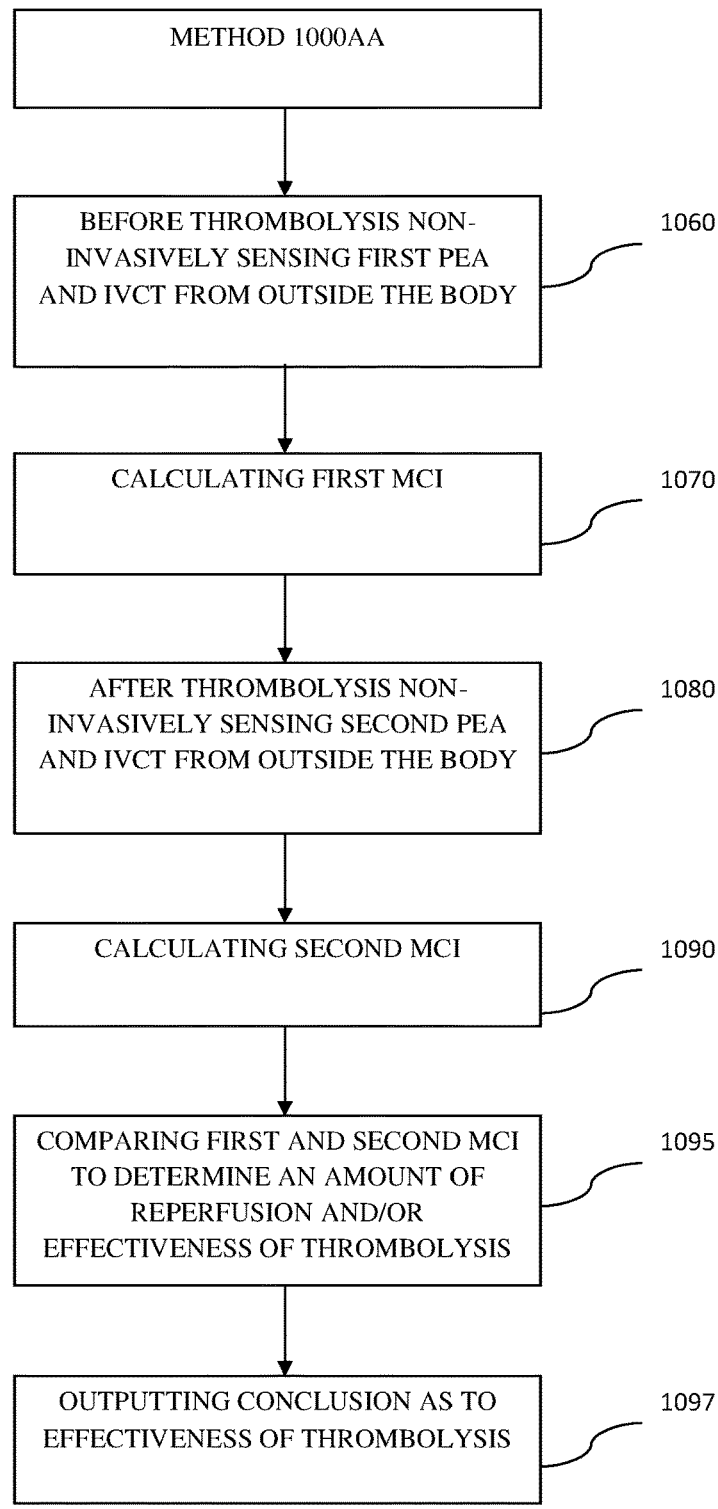
FIG. 11AA is a flow chart showing a yet still further method, in accordance with one embodiment of the invention.

The parallel method embodiment for assessing the effectiveness of thrombolysis based on the amount of reperfusion using the calculation of MCI is a method 1000AA (as shown in FIG. 11AA) of non-invasively assessing an effectiveness of thrombolysis on a clot, in an artery of a mammalian subject after a heart attack of the mammalian subject by determining an amount of reperfusion in the artery. The method 1000AA may comprise a step 1060 of, after a heart attack but before thrombolysis, non-invasively sensing by a device positioned outside the subject mechanical vibrations that are from a mechanical contraction of at least one of the ventricles of the heart of the mammalian subject, so as to simultaneously measure a first IVCT, wherein IVCT is a time duration of an isovolumetric contraction portion of a systole phase of a cardiac cycle of the subject, and a first peak endocardial acceleration (PEA) of the heart of the subject during the first IVCT. The method 1000AA may also comprise a step 1070 of calculating, by one or more processors, a first myocardial contractility index (MCI) of the subject, wherein the first MCI comprises a ratio of the first PEA of the subject to the first IVCT of the subject.

A further step 1080 of method 1000AA is, after the thrombolysis to dissolve the clot, non-invasively sensing by a device positioned outside the subject mechanical vibrations that are from a mechanical contraction of at least one of the ventricles of the heart of the mammalian subject, so as to simultaneously measure a second IVCT and a second peak endocardial acceleration (PEA) of the heart of the subject during the second IVCT;

A still further step 1090 may comprise calculating, by one or more processors, a second myocardial contractility index (MCI) of the subject wherein the second MCI comprises a ratio of the second. PEA of the subject to the second IVCT of the subject;

Method 1000AA may also include a step 1095 of determining, by one or more processors, an amount of reperfusion in the artery by comparing an amount by which the second MCI exceeds the first MCI.

Method 1000AA may also have a step 1097 of outputting, using an output unit 450, an alert or a quantitative (or other) assessment of the effectiveness of the thrombolysis in any form, including a difference between the first MCI and the second MCI in absolute amount or percentage or a ratio or other function, as well as any category or range describing the effectiveness (mildly effective moderately effective, very effectiveness, almost completely effective, completely effective, effective to the following numerical amount etc.). Since the effectiveness of the thrombolysis is based on or proportionate to the amount of reperfusion in the artery after the thrombolysis as compared to before the thrombolysis, the output may be in the form of an amount or percentage or other ratio of description of the reperfusion as described above in regard to other reperfusion embodiments. Method 1000AA may also include a step of determining, by the one or more processors, a degree of restoration function of the subject's heart derived from the thrombolysis.

As shown in FIG. 10, the invention, in one further embodiment, is a method 900 of determining an effectiveness of thrombolysis on a clot in an artery of a mammalian subject after a heart attack of the mammalian subject. Method 900 in some embodiments has a step 910 of during a first sensing period after a heart attack but before thrombolysis non-invasively sensing, for example by a device positioned outside the subject, mechanical vibrations that are from a mechanical contraction of at least one of the ventricles of the heart of the mammalian subject, so as to measure a first peak endocardial acceleration (PEA) of the heart of the subject during an IVCT wherein IVCT is a time duration of an isovolumetric contraction portion of a systole phase of a cardiac cycle of the subject.

Method 900 has a step 920 in some embodiments of, during a second sensing period after thrombolysis has been administered to dissolve the clot, non-invasively sensing mechanical vibrations that are from a mechanical contraction of at least one of the ventricles of the heart of the mammalian subject, so as to measure a second peak endocardial acceleration (PEA) of the heart of the subject during an IVCT. Method 900 has in some embodiments a step 930 of determining, by a processor, an amount by which the second PEA exceeds the first PEA, said amount determining the effectiveness of the thrombolysis. Note that method 900 does not include the administration of the thrombolysis as a step of the method. In some embodiments of method 900, the method includes a further step of determining, by a processor, that the second PEA exceeded the first PEA by at least two-tenths (or by at least a certain fraction wherein the certain fraction is within the range between one-tenth and three-tenths) so as to determine whether the thrombolysis has been effective (or in other embodiment determine how effective the thrombolysis has been).

As shown in FIG. 11, in a further embodiment, the invention is a method 1000 of determining an effectiveness of thrombolysis on a clot in an artery of a mammalian subject after a heart attack of the mammalian subject. Method 1000 has in some embodiments a step 1010 of during a first sensing period after a heart attack but before thrombolysis non-invasively sensing, for example by a device positioned outside the subject, mechanical vibrations that are from a mechanical contraction of at least one of the ventricles of the heart of the mammalian subject, so as to simultaneously measure (a) IVCT, wherein IVCT is a time duration of an isovolumetric contraction portion of a systole phase of a cardiac cycle of the subject; and (b) a peak endocardial acceleration (PEA) of the heart of the subject during the IVCT.

Method 1000 has a step 1020 in certain embodiments of calculating, by one or more processors, a first myocardial contractility index (MCI) of the subject, such that MCI comprises a ratio of the PEA of the subject to the IVCT of the subject. In some examples this ratio is MCI=k·PEA/IVCT, where k is a constant. In one such embodiment, k=1, such that the ratio is MCI=PEA/IVCT.

In some embodiments, the calculation in step 120 is derived from signals corresponding to the mechanical vibrations sensed during the first sensing period.

Method 1000 in some embodiments has a step 1030 of during a second sensing period after the thrombolysis non-invasively sensing, for example by a device positioned outside the subject, mechanical vibrations that are from a mechanical contraction of at least one of the ventricles of the heart of the mammalian subject, so as to simultaneously measure (a) a post-thrombolysis IVCT, wherein IVCT is a time duration of an isovolumetric contraction portion of a systole phase of a cardiac cycle of the subject; and (b) a peak endocardial acceleration (PEA) of the heart of the subject during the post-thrombolysis IVCT.

Method 1000 has a step 1040 in some embodiments of calculating, by the one or more processors, a second MCI of the subject for example from signals corresponding to the mechanical vibrations sensed during the second period. Method 1000 has a further step 1050 in some embodiments of determining, by the one or more processors, an amount by which the second PEA exceeds the first PEA, said amount determining whether the thrombolysis has been effective (or in other embodiments determine how effective the thrombolysis has been). In some embodiments, method 1000 also has a step of determining that the second MCI exceeded the first MCI by at least two-tenths (or by at least a certain fraction, wherein the certain fraction is in a range between one tenth and three-tenths, for example 15% or 17% or 22% or 25%) so as to determine the effectiveness of the thrombolysis.

A "processor" as used herein means a digital processor. In any embodiment of the invention, PEA can be measured and/or outputted in any suitable units of acceleration utilized by those skilled in the art, not just dP/dtmax, for example G or milig.

In this patent application, the phrase "a ratio of the PEA of the subject to the IVCT of the subject" or the "ratio of the PEA to the IVCT" of a subject or equivalent phrases are broad enough to include, at least in some embodiments, a linear or non-linear function of PEA as a substitute for PEA in the ratio and/or a linear or non-linear function of IVCT as a substitute for IVCT in the ratio. The following deviations from a simple ratio of PEA/IVCT are non-limiting, purely illustrative, examples that shall also be considered a ratio of the PEA to the IVCT of the subject: PEA/(IVCT plus c), where c is a constant; or (PEA+e)/IVCT, where c is a constant; or 2·PEA/IVCT; or PEA/(0.7·IVCT); or (2·PEA+c)/(0.7·IVCT−2c); or $PEA^{(1.5)}/(IVCT^{(0.8)}+c)$ where c is a constant.

While the invention has been described with respect to a limited number of embodiments, it will be appreciated that many variations, modifications and other applications of the invention may be made. Therefore, the claimed invention as recited in the claims that follow is not limited to the embodiments described herein.

What is claimed is:

1. A non-invasive apparatus configured to non-invasively determine an amount of reperfusion of blood to a myocardium supplied by an artery of a mammalian subject after a heart attack of the mammalian subject, the apparatus comprising:
- a sensor unit configured to non-invasively sense from outside the subject mechanical vibrations that are from a mechanical contraction of at least one of the ventricles of the heart of the mammalian subject so as to simultaneously measure
  - (a) IVCT, wherein IVCT is a time duration of an isovolumetric contraction portion of a systole phase of a cardiac cycle of the subject; and
  - (b) a peak endocardial acceleration (PEA) of the heart of the subject during the IVCT; and
- a determination unit comprising one or more processors programmed by software stored on a memory, the determination unit configured to receive digital signals corresponding to the sensed mechanical vibrations, and to determine the PEA during the IVCT,
- the determination unit including a perfusion module for determining, by the one or more processors and the software, an amount of reperfusion in the myocardium by comparing a first PEA of the subject sensed by the sensor unit after a heart attack but before opening the artery to a second PEA of the subject sensed by the sensor unit at a subsequent time after opening the artery,
- the software also programmed to determine from the amount by which the second PEA exceeds the first PEA, whether a myocardium that was at risk from the heart attack was salvaged, said amount of reperfusion being proportionate to an amount of the myocardium that was salvaged.

2. The apparatus of claim 1, wherein the determination unit is configured to determine a degree of restoration of function of the subject's heart derived from the opening of the artery.

3. A non-invasive apparatus configured to non-invasively determine an amount of reperfusion of blood to a myocardium supplied by an artery of a mammalian subject after a heart attack of the mammalian subject, the apparatus comprising:
- a sensor unit configured to non-invasively sense from outside the subject mechanical vibrations that are from a mechanical contraction of at least one of the ventricles of the heart of the mammalian subject so as to simultaneously measure
  - (a) IVCT, wherein IVCT is a time duration of an isovolumetric contraction portion of a systole phase of a cardiac cycle of the subject; and
  - (b) a peak endocardial acceleration (PEA) of the heart of the subject during the IVCT; and
- a determination unit comprising one or more processors programmed by software stored on a memory, the determination unit configured to receive digital signals corresponding to the sensed mechanical vibrations, and to determine the PEA during the IVCT, the one or more processors configured to also calculate a first myocardial contractility index (MCI) of the subject such that MCI comprises a ratio of the PEA of the subject to the IVCT of the subject;
- the determination unit including a perfusion module for determining, by the one or more processors, an amount of reperfusion in the myocardium by comparing a first MCI of the subject sensed by the sensor unit after a heart attack but before opening the artery to a second MCI of the subject sensed by the sensor unit at a subsequent time after opening the artery,
- the software also programmed to determine from the amount by which the second MCI exceeds the first MCI, whether a myocardium that was at risk from the heart attack was salvaged, said amount of reperfusion being proportionate to an amount of the myocardium that was salvaged.

4. The apparatus of claim 3, wherein the determination unit is configured to determine a degree of restoration of function of the subject's heart derived from the opening of the artery.

* * * * *